(12) United States Patent
Shinozaki et al.

(10) Patent No.: US 7,842,854 B2
(45) Date of Patent: Nov. 30, 2010

(54) GENES ENCODING PLANT TRANSCRIPTION FACTORS

(75) Inventors: Kazuko Shinozaki, Ibaraki (JP); Yusuke Ito, Ibaraki (JP); Yoh Sakuma, Ibaraki (JP)

(73) Assignees: International Research Center for Agricultural Sciences, Ibaraki (JP); Incorporated Administrative Agency, National Agriculture and Bio-oriented Research Organization, Ibaraki (JP)

( * ) Notice: Subject to any disclaimer, the term of this patent is extended or adjusted under 35 U.S.C. 154(b) by 785 days.

(21) Appl. No.: 11/453,724

(22) Filed: Jun. 15, 2006

(65) Prior Publication Data

US 2006/0230471 A1  Oct. 12, 2006

Related U.S. Application Data

(62) Division of application No. 10/302,382, filed on Nov. 22, 2002, now Pat. No. 7,138,277.

(30) Foreign Application Priority Data

Nov. 22, 2001  (JP) .............................. 2001-358268

(51) Int. Cl.
*C12N 15/29* (2006.01)
*C12N 15/82* (2006.01)
(52) U.S. Cl. .................... 800/289; 435/320.1; 435/419; 536/23.6; 800/298
(58) Field of Classification Search ........................ None
See application file for complete search history.

(56) References Cited

U.S. PATENT DOCUMENTS

| 5,891,859 | A | 4/1999 | Thomashow et al. |
| 6,495,742 | B1 | 12/2002 | Shinozaki et al. |
| 6,670,528 | B1 * | 12/2003 | Shinozaki et al. ........... 800/298 |

FOREIGN PATENT DOCUMENTS

| JP | 2000-060558 | 2/2000 |
| JP | 2000-116260 | 4/2000 |

OTHER PUBLICATIONS

Abe, et al., "Role of Arabidopsis MYC and MYB Homologs in Drought and Abscisic Acid-Regulated Gene Expression", The Plant Cell, vol. 9, pp. 1859-1868, Oct. 1997.
Abstract: Liu, Qiang, et al., Analysis of DREB Gene Encoding a Protein Binding to the cis-Element DRE which Stimulates Dehydration/Low Temperature Stress-Responsive Gene Expression in Arabidopsis Thaliana. 1998 Annual Meeting and the 38th Symposium of the Japanese Society of Plant Physiologists, May 3-5, 1998, F3a-11.
Abstract: Miura, Setsuko, et al., Analysis of Arabidopsis Thaliana, in which the Dehydration/Salt/Low-Temperature Stress Inducible Transcription Factor DREB1A or DREB2A is Over-expressed. 1998 Annual Meeting and the 38th Symposium of the Japanese Society of Plant Pathologists, May 3-5, 1998, F3a-12.
Abstract: Shirjwari, Zabta K., et al., Identification of the DREB1B Family Encoding Proteins which Bind to the Dehydration/Low Temperature Responsive Element DRE of Arabidopsis Thaliana and Analysis of Expression of The family. 1998 Annual Meeting and the 38th Symposium of the Japanese Society of Plant Pathologists, May 3-5, 1998, F3a-13.
Busk, et al., "Regulatory elements in vivo in the promoter of the abscisic acid responsive gene reb17 from maize", The Plant Journal, vol. 11, No. 6, 1997, pp. 1285-1295.
Jiang, et al., "Requirement of a CCGAC cis-acting element for cold induction of the BN115 gene from winter Brassica napus", Plant Molecular Biology, vol. 30, 1996, pp. 679-684.
Liu, et al., "Two Transcription Factors, DREB1 and DREB2, with an EREBP/AP2 DNA Binding Domain Sep. TwoCell. Signal Transduction Pathways in Drought-and Low-Temp-Respon. Gene Express., Respectively, in Arabidopsis", Aug. 1998, The Plant Cell, V. 10, p. 1391-1406.
Quellet, et al., "The wheat wcs 120 promoter is cold-inducible in both monocotyledonous and dicotyledonous species", Federation of European Biochemical Societies Letters, vol. 423, 1998, pp. 324-328.
Riechmann et al., "Arabidopsis transcription factors: genome-wide comparative analysis among eukaryotes", Science, Dec. 15, 2000, vol. 290, pp. 2105-2110.
Sambrook, et al., "Molecular Cloning, A Laboratory Manual", Second Edition, Cold Spring Harbor Laboratory Press, 1989, pp. 11.45-11.55.
Shinozaki, et al. "A Novel cis-Acting Element in an Arabidopsis Gene is involved in Responsiveness to Drought, Low-Temperature, or High-Salt Stress", The Plant Cell, vol. 6, pp. 251-264, Feb. 1994.
"The 8th JIRCAS International Symposium, Program and Abstracts", Japan International Reasearch Center for Agricultural Sciences, Nov. 27 and 28, 2001, P-07.
Sambrook, et al.; Molecular Cloning, A Laboratory Manual, Second Edition; Cold Spring Harbor Laboratory Press, 1989, pp. 11.45-11. 55.

* cited by examiner

*Primary Examiner*—David H Kruse
(74) *Attorney, Agent, or Firm*—Davidson, Davidson & Kappel, LLC

(57) ABSTRACT

Identification of a gene from monocotyledonous plants such as rice, which codes for a transcription factor specific to a stress tolerant gene and provision of a novel environmental stress tolerant plant using the gene. From the rice genome, a gene, which binds to a cis element existing upstream of the gene encoding a stress responsive protein and for a transcription factor to activate the transcription of the gene, is identified. Further, the gene of the transcription factor is used to transform a plant, thereby improving tolerance against environmental stresses such as low temperature, dehydration, and salt stresses.

22 Claims, 9 Drawing Sheets
(1 of 9 Drawing Sheet(s) Filed in Color)

FIG. 1
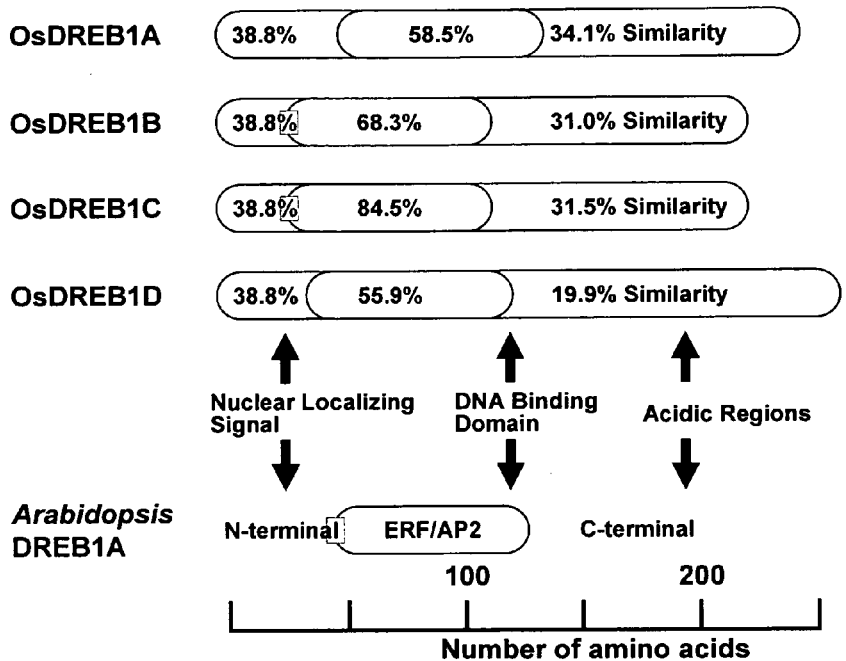
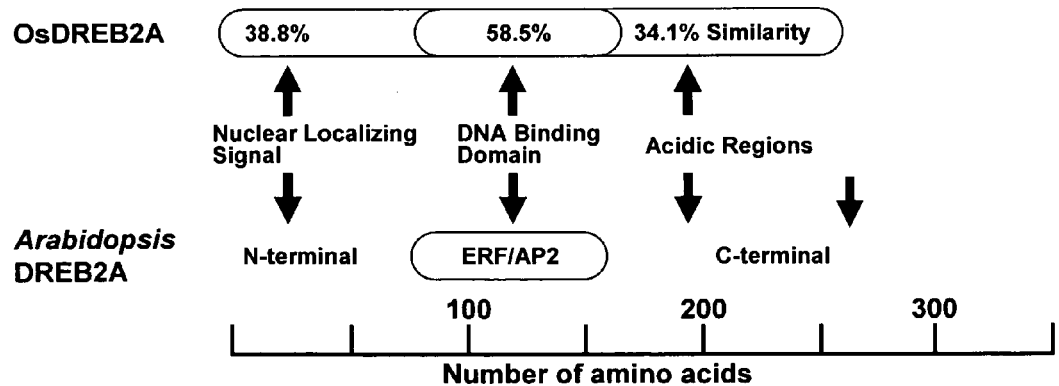

FIG. 2

```
OsDREB1A   1:..............................MCGIKQEMSGESSGSPCSSASAERQHQTVWTAP
OsDREB1B   1:.................................................MEVEEAAYRTVWSEP
OsDREB1C   1:...............................................MEYYEQEEYATVT.....SAP
OsDREB1D   1:...........................................MEKNTAASGQLMTSSAEATP
BCBF3      1:MSPTLSLKLKKSSHTPQSSVSSSTMLRLFKKEAACQSPSTLPVAMDMGLEVSSSSPSSSVSSSP
DREB1A     1:...............................MNSFSAFSEMFGSDYESSVSSGGDYIP
ACRE111B   1:....................................MDIFRSYYSDPLAEYSSISDSSSSSCN
AF084185   1:............................MTSFSTFSEMLGSEYESPVTLGGEYCP

OsDREB1A   33:..............PKRPAGRTKFRETRHPVFRGVRRRGN....AGRWVCEVRVPGRRGCRLWL
OsDREB1B   15:..............PKRPAGRTKFRETRHPVYRGVRRRGGRPGAAGRWVCEVRVPGARGSRLWL
OsDREB1C   16:..............PKRPAGRTKFRETRHPVYRGVRNRG....CAGRWVCKVRVPGSRGDRFWI
OsDREB1D   20:............SSPKRPAGRTKFCETRHLVFRGVRRRGP....AGRWVCEVRREPNKK.SRIWL
BCBF3      65:......EHAARRASPAKRPAGRTKFRETRHPVYRGVRRRN....TERWVCEVRVPGKRGARLWL
DREB1A     27:.........TLASSCPKKPAGRKKFRETRHPIYRGVRRRN.....SGKWVCEVREPNKK.TRIWL
ACRE111B   28:RANHSDEEVMLASNNPKKRAGRKKFRETRHPVYRGVRKRN.....SDKWVCELREPNKK.SRIWL
AF084185   27:........KLAASCPKKPAGRKKFRETRHPVYRGVRLRN.....SGKWVCEVREPNKK.SRIWL

OsDREB1A   80:GTFDTAEGAARAHDAAMLAINAGGGGGGGACCLNFADSAWLLAVPRSYRTLR..RRPPRRAEAVE
OsDREB1B   66:GTFATAEAAARAHDAAALALRG......RAACLNFADSAWRMPPVPASAALAGARGVRDAVAVAV
OsDREB1C   63:GTSDTAEETARTHDAAMLALRGR......GACLNFADSARLLRVDPATLATPD..DIRRAAIELA
OsDREB1D   68:GTFATAEAAARAHDVAALALCG......ASASLNFADSAWLLHVPRAPVVSGLRPPAARCATRCL
BCBF3     121:GTYATAEVAARANDAAMLALGGRS.....ATCLNFADSAWLLAVPSALSDLA...DVRRAAVEAV
DREB1A     78:GTFQTAEMAARAHDVAALALRGR......SACLNFADSAWRLRIPESTCAK...DIQKAAAAEAA
ACRE111B   87:GTFPSAEMAARAHDVAATALRGR......SACLNFADSAWKLPIPASTDAK....DIQKAAAEAA
AF084185   78:GTFLTAEIAARAHDVAAIALRGK......SACLNFADSAWRLRIPETTCPK....EIQKAAAEAA

OsDREB1A  143:DFFRRRLADDALSATSSSSTTPSTPRTDDDEESAATDGDESSSP............ASDLAFELD
OsDREB1B  125:EAFQRQSAAPSSPAETFANDGDEEEDNKDVLPVAAAEVFDAGAF...........ELDDGFRFG
OsDREB1C  120:ESCPHDAAAAAASSSAAAVEASAAAAPAMMMQYQDDMAATPSSYD...............YAYYG
OsDREB1D  127:QGHRRVPAPGRGSTATATATSGDAASTAPPSAPVLSAKQCEFIFLSSLDCWMLMSKLISSSRAKG
BCBF3     178:ADFQRREAADGSLAIAVPKEASSGAPSLSPSSGSDSAGSTGTSEPSANGVFEGPVVMDSEMFRLD
DREB1A    133:LAFQDEMCDATTDHGFDMEET..........LVEAIYTAEQSEN..............AFYMH
ACRE111B  142:EAFRSSEAENMPEY...SGE................DTKEVNSTPEN..............MFYMD
AF084185  133:LAFQAEINNTTTDHGLDMEET...........IVEAIFTEENND................VFYMD

OsDREB1A  196:VLSDMG........WDLYYASLAOGMLNEPPSA....ALGDDGDAILADVPLWSY......
OsDREB1B  178:GMDAG..........SYYASLAOGLLVEPPAAG...AWWEDGELAGSDMPLWSY......
OsDREB1C  170:NMDFDQ........PSYYYDGMGGGEYQSWQ.MDGDDDGGAGGYGGGDVTLWSY......
OsDREB1D  192:SLCLRKNPISFCMVTNSYTRLLLEYIILQMNSMIVLIHELSKYQVFLLLTMITHHLFQWRR
BCBF3     243:LFPEMD........LGSYYMSLAEALCMDPPPTATIIHAYEDNGDGGADVRLWSYSVDM..
DREB1A    172:DEAMFE........MPSLLANMAEGMLLPLPS.VQWNHNHEVGDG.DDDVSLWSY.......
ACRE111B  175:EEALFP........MPGLLVNMAEGLMLPPP...QCSQIGDHMEA.DVDMPLWSYSI....
AF084185  171:EESMLE........MPALLRSMAEGMLPPPS.VHFGHNYDFDG..DADVSLWSY.......
```

AMINO ACID SEQUENCE OF DREB1-HOMOLOGOUS PROTEIN

FIG. 3

```
OsDREB2A    1:..MERGEGRRGDCSVQVRKKRTRRKSDGPDSIAETIKWKEQNQKLQEENSSR...KAPAKGSKK
DREB2A      1:MAVYDQSGDRNRTQIDTSRKRKSRSRGDGTTVAERLKRWKEYNETVEEVSTKK..RKVPAKGSKK
ORCA1       1:MALLDQASNLSPMPFDFTRKRKSRRRDGTKNVAETLAKWKEYNEKLDALDGGKPARKVPAKGSKK

OsDREB2A   61:GCMAGKGGPENSNCAYRGVRQRTWGKWVAEIREPNRGRRLWLGSFPTALEAAHAYDEAARAMYGP
DREB2A     64:GCMKGKGGPENSRCSFRGVRQRIWGKWVAEIREPNRGSRLWLGTFPTAQEAASAYDEAAKAMYGP
ORCA1      66:GCMKGKGGPENSHCKYRGVRQRTWGKWVAEIREPNRGSRLWLGTFRNAIEAALAYDEAARAMYGP

OsDREB2A  126:TARVNFADNSTDANSGCTSAPSLMMSNGPATIPSDEKDE.LESPPFIVANGP.......AVLYQP
DREB2A    129:LARLNFPRSDASEVTSTSSQSEVCTVETPGCVHVKTEDPDCESKPFSGGVEP...MYCLENGAEE
ORCA1     131:CARLNLPNYRASEESSSLPTTSGSDTTTASGISEVSVYEDKKFTPVVSGLKQDDKGESLESADSK

OsDREB2A  182:......D.KKDVLERVVPEVQDVKTEGSN........GLKRVCQERKNMEVCESEGIVLHKEVNI
DREB2A    191:MKRGVKADKHWLSEFEHNYWSDILKEKEK....QKEQGIVETCQQQQQDSLSVADYGWPNDVDQS
ORCA1     196:PQLLVDAGTPMSAVKEEPKEYQVMDSQSEGQFGDEPPSKLVCKEVDFGQDQAVVPAVKNAEEMG

OsDREB2A  233:SYDY.........FNVHEVVEMIIVELSADQKTEVHEEYQEGDDGFSLFSY..............
DREB2A    252:HLDS.........SDMFDVDELLRDLNGDDVFAGLNQDRYP.GNSVANGSYRPE...........
ORCA1     261:GEMGGDILKGCSLSEMFDVDELLSVLDSTPLHASDFQHGMGNGNVKAEAAPNYAPSWDSAFQLQN

OsDREB2A      :..............................................................
DREB2A    295:.......SQQSGFDPLQSLNYGIPPFQLEGK.DGNGFFDDLSYLDLEN....
ORCA1     326:QDPKLGSQQHMAQTPPEINSGLDFLQPGRQEDSYFTLGDLDFLDLGAELGL
```

AMINO ACID SEQUENCE OF DREB2-HOMOLOGOUS PROTEIN

FIG. 5
(A)
EFFECTOR PLASMID
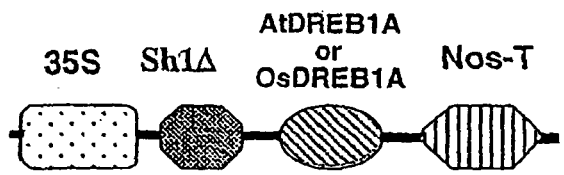
REPORTER PLASMID
(B)
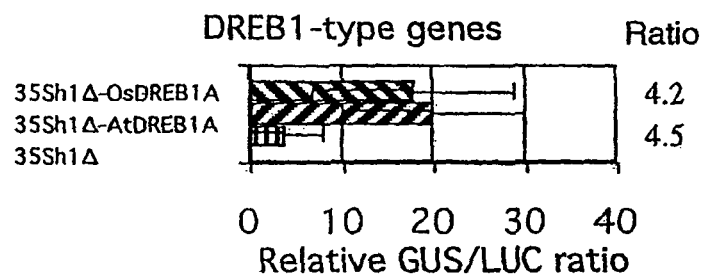
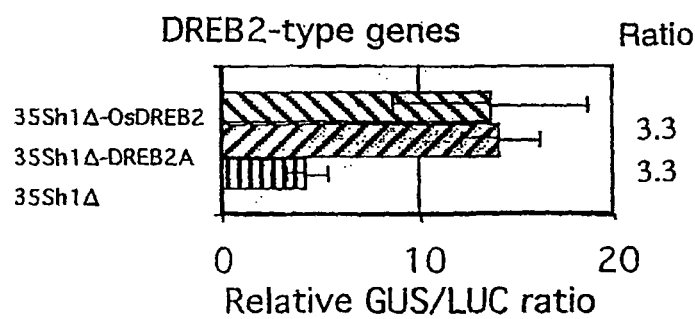

ANALYSIS OF OsDREB GENE EXPRESSION BY THE NORTHERN METHOD

GENES ENCODING PLANT TRANSCRIPTION FACTORS

CROSS REFERENCE TO RELATED APPLICATION

This application is a divisional of U.S. patent application Ser. No. 10/302,382, filed Nov. 22, 2002.

BACKGROUND OF THE INVENTION

1. Field of the Invention

The present invention relates to a protein, which regulates rice-derived environmental stress tolerance, a gene encoding the same, and a method for utilizing the same.

2. Prior Art

Plants possess tolerance mechanisms to cope with various types of environmental stresses in nature such as dehydration, high temperature, freezing, or salt stress. In the production of plants having such environmental stress tolerance, techniques have been heretofore used for genetically selecting and mating strains which are dehydration, salt, or low temperature tolerant. However, these techniques require long periods of time to select, and also have low success rates.

On the other hand, as the stress tolerance mechanism is elucidated at a molecular level, stress tolerant plants have been produced using biotechnological techniques. For example, it has been shown that stress proteins such as LEA proteins, water channel proteins, or synthetases for compatible solutes are induced in cells when they are exposed to stress, thereby protecting the cells from such stress. Thus, research has been attempted in which genes such as LEA proteins of barley or detoxification enzymes of tobacco, or genes of synthetases for osmoregulatory substances (e.g., sugar, proline, or glycinebetaine) are introduced into host plants. Research using genes encoding w-3 fatty acid desaturase of *Arabidopsis thaliana*, the D9-desaturase of blue-green algae, or the like, which are modification enzymes of the cellular membrane lipid, has also been attempted. In the above researches, a gene was bound to the 35S promoter of cauliflower mosaic virus and introduced into a plant. The level of stress tolerance of the recombinant plant was, however, low and unstable. Thus, none of these was put to practical use.

On the other hand, stress tolerance mechanism is found to be intricately associated with several genes (Plant Physiol., 115: 327-334 (1997)). Accordingly, research in which a gene encoding a transcription factor which simultaneously activates the expression of the genes is introduced into a plant, thereby enhancing the plant's stress tolerance, has been attempted (The Plant Cell, 10: 1-17 (1998)). However, when several genes are simultaneously activated, the energy of the host plant becomes directed towards the generation of the gene product or intracellular metabolism resulting from the gene product. Accordingly, the growth of the plant itself deteriorates or becomes retarded.

In contrast, the present inventors had isolated the genes DREB1A, DREB1B, DREB1C, DREB2A, and DREB2B encoding the transcription factors which bind to a stress responsive element and specifically activate the transcription of genes located downstream of the element from *Arabidopsis thaliana* (Japanese Patent Application No. 10-22847, Laying-Open (kokai) No. 2000-60558). They reported that introduction and overexpression of the genes in a plant enabled impartment of stress tolerance without causing retardation of a plant (Japanese Patent Application No. 10-292348, Laying-Open (kokai) No. 2000-116260).

*Arabidopsis thaliana* is classified as a dicotyledonous plant while major crops such as rice, maize, and wheat are classified as monocotyledonous plants. Dicotyledonous plants are relatively different from monocotyledonous plants from the viewpoint of plants evolution. It has been shown that the DREB1A gene of *Arabidopsis thaliana* functions well in monocotyledonous plants, but not as well in dicotyledonous plants. Thus, if a DREB-homologous gene derived from the monocotyledonous plant can be isolated, environmental stress tolerance can be more efficiently transmitted to monocotyledonous plants thereby.

SUMMARY OF THE INVENTION

An object of the present invention is to identify from a monocotyledonous plant such as rice, a gene which codes for a transcription factor specific to a stress tolerant gene, and to provide a novel environmental stress tolerant plant using the same gene.

The present inventors have conducted concentrated studies in order to attain the above object. As a result, they had succeeded in identifying all the DREB-homologous genes from the rice genome. They also found that introduction of the genes into other plants significantly enhanced their environmental stress tolerance. This has led to the completion of the present invention.

More specifically, the present invention provides the following (1) to (12).

(1) An isolated gene comprising the following DNA (a) or (b):
 (a) DNA which comprises the nucleotide sequence as shown in SEQ ID NO: 1, SEQ ID NO: 3, SEQ ID NO: 5, SEQ ID NO: 7, or SEQ ID NO: 9; or
 (b) DNA which hybridizes with the DNA comprising a nucleotide sequence, which is complementary to the DNA comprising the nucleotide sequence as shown in SEQ ID NO: 1, SEQ ID NO: 3, SEQ ID NO: 5, SEQ ID NO: 7, or SEQ ID NO: 9 under stringent conditions and which codes for a protein that regulates the transcription of genes located downstream of a stress responsive element.

(2) An isolated gene encoding the following protein (c) or (d):
 (c) a protein which comprises the amino acid sequence as shown in SEQ ID NO: 2, SEQ ID NO: 4, SEQ ID NO: 6, SEQ ID NO: 8, or SEQ ID NO: 10; or
 (d) a protein which comprises the amino acid sequence having deletion, substitution, or addition of one or several amino acids in the amino acid sequence as shown in SEQ ID NO: 2, SEQ ID NO: 4, SEQ ID NO: 6, SEQ ID NO: 8, or SEQ ID NO: 10 and which regulates the transcription of genes located downstream of a stress responsive element.

(3) The gene according to (1) or (2) above, wherein the stress is dehydration stress, low temperature stress, or salt stress.

(4) The following recombinant protein (c) or (d):
 (c) a protein which comprises the amino acid sequence as shown in SEQ ID NO: 2, SEQ ID NO: 4, SEQ ID NO: 6, SEQ ID NO: 8, or SEQ ID NO: 10; or
 (d) a protein which comprises the amino acid sequence having deletion, substitution, or addition of one or several amino acids in the amino acid sequence as shown in SEQ ID NO: 2, SEQ ID NO: 4, SEQ ID NO: 6, SEQ ID NO: 8, or SEQ ID NO: 10 and which regulates the transcription of genes located downstream of a stress responsive element.

(5) The protein according to (4) above, wherein the stress is dehydration stress, low temperature stress, or salt stress.

(6) A recombinant vector comprising the gene according to any one of (1) to (3) above.

(7) A transformant transformed with the recombinant vector according to (6) above.

(8) The transformant according to (7) above, wherein the host is a plant.

(9) The transformant according to (7) above, wherein the host is a monocotyledonous plant.

(10) A method for producing a protein which regulates the transcription of genes located downstream of a stress responsive element, wherein the transformant according to (8) or (9) above is cultured in a medium and the protein is recovered from the resultant culture product.

(11) A method for determining stress levels in plants, wherein the transcription levels of the gene according to any one of (1) to (3) above in plant bodies are determined.

(12) A method for improving the stress tolerance of plants by introducing the gene according to any one of (1) to (3) above into the plants.

The present invention provides a stress tolerant transcription factor derived from monocotyledonous plants and a gene encoding this transcription factor. Use of the gene according to the present invention enables the more efficient transmission of stress tolerance to crops, i.e., monocotyledonous plants.

BRIEF DESCRIPTION OF THE DRAWINGS

The patent or application file contains at least one drawings executed in color. Copies of this patent or patent application publication with color drawings will be provided by the Office upon request and payment of the necessary fee.

FIG. 1 shows a structure of the OsDREB protein (A: OsDREB1, B: OsDREB2).

FIG. 2 shows an amino acid sequence of a DREB1-homologous protein (OsDREB1A, OsDREB1B, OsDREB1C, OsDREB1D; rice, BCBF3; barley, DREB1A; *Arabidopsis thaliana*, ACRE111B; tobacco).

FIG. 3 shows an amino acid sequence of a DREB2-homologous protein (OsDREB2A; rice, DREB2A: *Arabidopsis thaliana*, ORCA1; *Catharanthus roseus*).

FIG. 5(A) shows the structure of a plasmid used in transactivation, and FIG. 5(B) shows a ratio of introduction efficiency by transactivation (GUS/LUC).

DETAILED DESCRIPTION OF THE INVENTION

Figure 4:
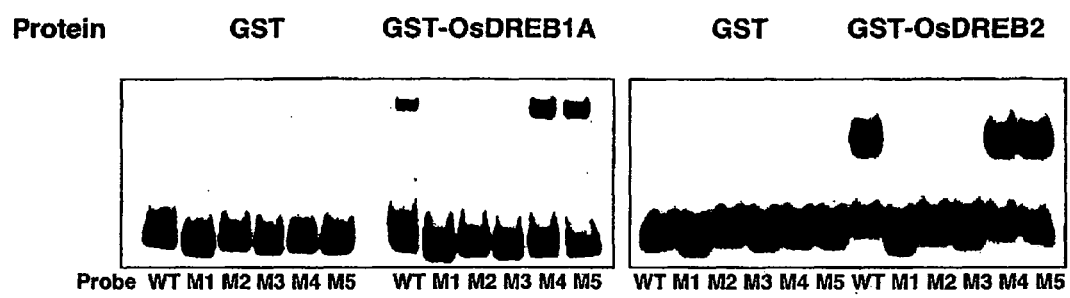
FIG. 4 shows the result of a gel shift assay.

This specification includes part or all of the contents as disclosed in the specification of Japanese Patent Application No. 2001-358268, which is a priority document of the present application.

The gene according to the present invention is a gene derived from rice genome having tolerance improving mechanisms against environmental stresses such as low temperature, dehydration, or salt stress.

The gene of the present invention is "an isolated gene encoding a transcription factor which binds to a cis element located upstream of genes encoding stress responsive proteins expressed in response to environmental stresses such as low temperature, dehydration, or salt stress, thereby activating the transcription of the genes". Specific examples of the above cis element include dehydration-responsive element (DRE), abscisic acid-responsive element (ABRE), and low temperature-responsive element. The protein encoded by the gene of the present invention functions to activate the transcription of genes located downstream of the above-mentioned stress responsive elements (DRE or the like).

The gene according to the present invention can be identified as, for example, described below.

1. Identification of the Gene of the Present Invention

The gene according to the present invention can be screened based on homology with a known gene having homologous functions, that is, a gene encoding a transcription factor specific to a stress tolerant gene of a plant. mRNA and cDNA libraries of rice or a rice genomic library may be prepared and may be subjected to screening. Alternatively, an existing database of rice DNA may be subjected to screening.

A. Screening of Gene Library (1) Preparation of mRNA and cDNA Libraries

At the outset, mRNA and cDNA libraries are prepared as follows.

As a source of mRNA, parts of the plant body of rice such as leaves, stems, roots, or flowers, or the plant body as a whole may be used. Alternatively, a plant body obtained by sowing rice seeds on a solid medium such as GM medium, MS medium, or #3 medium and growing them aseptically may be used. The source may be a callus or a cultured rice cell which was aseptically grown, and the variety thereof is not particularly limited as long as the cell contains mRNA of the gene of interest. Further, since the gene to be screened is expressed in response to environmental stress, plants that are exposed to low temperature stress (e.g. 10 to −4° C.), salt stress (e.g. 150 to 250 mM NaCl), or dehydration stress (e.g. dehydrated state) can also be preferably used.

For example, mRNA is prepared as follows. Rice plant bodies, which had been grown hydroponically to low temperature stress, dehydration stress, or salt stress are exposed and then freezed with liquid nitrogen. The frozen plant bodies are ground in a mortar. From the resultant ground material, crude RNA fraction is extracted and prepared by the glyoxal method, the guanidine thiocyanate-cesium chloride method, the lithium chloride-urea method, the proteinase K-deoxyribonuclease method, or the like. From this crude RNA fraction, poly(A)+RNA (mRNA) can be then obtained by the affinity column method using oligo dT-cellulose or poly U-Sepharose carried on Sepharose 2B or by the batch method. The resultant mRNA may further be fractionated by sucrose density gradient centrifugation or the like.

Further, a cDNA library can be produced using the thus obtained mRNA as a template. For example, single-stranded cDNA is synthesized using an oligo(dT) primer or random primer, and a reverse transcriptase in a commercially available kit (e.g. ZAP-cDNA Synthesis Kit: Stratagene). Then, double-stranded cDNA is synthesized from the resultant single-stranded cDNA. Subsequently, an adaptor containing a suitable restriction site is added to the resultant double-stranded cDNA, which is then inserted into a cloning site of a lambda phage vector. The resultant DNA is packaged using Gigapack III Gold packaging extract (Stratagene) or the like and infected into an *E. coli* host, and then amplified. Thereafter, phage particles are recovered and stored.

(2) Preparation of Genomic Library

For example, the preparation of a genomic library using a lambda phage vector is carried out in the following manner. As a source of DNA, parts of the rice plant body such as leaves, stems, roots, or flowers, or the plant body as a whole may be used as long as the tissue contains DNA. The plant body is pulverized in the presence of liquid nitrogen, and DNA is extracted by the CTAB method, the benzyl chloride method, or the like. The resultant DNA is partially decomposed with the restriction enzyme Sau3AI and then fractionated by NaCl density gradient ultracentrifugation or the like to recover 10 to 20 kb fragments. These fragments are inserted into the BamHI cleavage site of lambda phage vectors such as λEMBL3 and λFIX II. Thereafter, packaging is carried out using Gigapack III Gold packaging extract (Stratagene) or the like, followed by infection into an *E. coli* host. The amplified phage particles are then recovered and stored.

(3) Screening of Library

A library can be screened in the following manner.

A DNA fragment as a probe is prepared based on a sequence in a highly conserved region of, for example, a known gene encoding a transcription factor specific to a stress tolerant gene of a plant, such as the DREB gene derived from *Arabidopsis thaliana* (DREB1A gene: SEQ ID NO: 11, DREB2A gene: SEQ ID NO: 12, DREB1B gene: SEQ ID NO: 13, DREB1C gene: SEQ ID NO: 14, DREB2B gene: SEQ ID NO: 15). The probe DNA may be amplified by PCR using two primers with approximately 15 bp to 25 bp which are designed based on the sequence of each side of the highly conserved region so as to amplify said region. When the highly conserved region is short and insufficient as a probe, a primer may be designed to amplify several highly conserved regions together with the regions adjacent thereto.

Using the above probe, a cDNA library or genomic library is screened by plaque hybridization or colony hybridization.

B. Screening Using Gene Database

Important sequences (highly conserved regions or regions deduced to have desired function) of, for example, a known gene that encodes a transcription factor specific to a stress tolerant gene of a plant such as DREB gene derived from *Arabidopsis thaliana* (DREB1A gene, DREB1B gene, DREB1C gene, DREB2A genes, DREB2B gene) are specified. Subsequently, homology search on an existing gene database is conducted based on the specified sequence. The genetic data to be searched may be EST or a full-length gene. Homology search can be carried out using an analytical software such as BLAST or FASTA on databases of GenBank or DDBJ. Preferably, the object of detection is a gene encoding an amino acid sequence which has an especially high homology with an amino acid sequence in the highly conserved region or a region deduced to have desired function, consequently a sequence conserving an amino acid sequence that is essential for the function of a protein. Based on the resultant sequence, a primer is designed, and PCR is carried out using uncloned cDNA (RT-PCR), a cDNA library, genomic DNA, or a genomic library as a template, thereby obtaining the gene of interest. Alternatively, a DNA fragment amplified by PCR is used as a probe and a cDNA library or genomic library is screened to obtain the gene of interest.

C. Determination of Nucleotide Sequences

The entire nucleotide sequence of the cloned cDNA can be determined in accordance with conventional methods. Nucleotide sequencing includes the chemical modification method of Maxam-Gilbert or the dideoxynucleotide chain termination method using M13 phage. Usually, sequencing is carried out using an automated nucleotide sequencer (e.g., 377 DNA Sequencer, Perkin-Elmer).

Thus, OsDREB1A (SEQ ID NO: 1), OsDREB1B (SEQ ID NO: 3), OsDREB1C (SEQ ID NO: 5), OsDREB1D (SEQ ID NO: 7), and OsDREB2A (SEQ ID NO: 9) were identified as DREB-homologous genes derived from rice.

Also, OsDREB1A protein (SEQ ID NO: 2), OsDREB1B protein (SEQ ID NO: 4), OsDREB1C protein (SEQ ID NO: 6), OsDREB1D protein (SEQ ID NO: 8), and OsDREB2A protein (SEQ ID NO: 10), which were coded by the genes through analysis of ORFs of the genes, were identified.

The genes according to the present invention, however, are not limited to genes comprising DNA as shown in SEQ ID NO: 1, SEQ ID NO: 3, SEQ ID NO: 5, SEQ ID NO: 7, or SEQ ID NO: 9. Genes comprising DNA, which are hybridizable under stringent conditions with DNA comprising a nucleotide sequence that is complementary to the DNA comprising a nucleotide sequence as shown in SEQ ID NO: 1, SEQ ID NO: 3, SEQ ID NO: 5, SEQ ID NO: 7, or SEQ ID NO: 9, are also genes of the present invention as long as they code for proteins that regulate the transcription of genes located downstream of a stress responsive element.

The term "stringent conditions" as used herein refers to parameters with which the art is familiar. Stringent conditions are sequence-dependent and will be different in different circumstances. Longer sequences hybridize specifically at higher temperatures. Generally, stringent conditions are selected to be about 5° C. lower than the thermal melting point $(T_m)$ for the specific sequence at a defined ionic strength and pH. The $T_m$ is the temperature (under defined ionic strength, pH and nucleic acid concentration) at which 50% of the probes complementary to the target sequence hybridize to the target sequence at equilibrium. Nucleic acid hybridization parameters may be found in references which compile such methods, e.g., Molecular Cloning: A Laboratory Manual, J. Sambrook, et al., eds., Second Edition, Cold Spring Harbor Laboratory Press, Cold Spring Harbor, N.Y., 1989. More specifically, stringent conditions, as used herein, refers, for example, to those conditions in which formamide concentration is 30-50%, temperature is 37 to 50° C., and 6×SSC. Preferably, formamide concentration is 50%, temperature is 42° C., and 6×SSC.

The genes of the present invention are genes encoding proteins comprising amino acid sequences as shown in SEQ ID NO: 2, SEQ ID NO: 4, SEQ ID NO: 6, SEQ ID NO: 8, or SEQ ID NO: 10. Even though a protein comprises an amino acid sequence having deletion, substitution, or addition of one or several amino acids in the amino acid sequence as shown in SEQ ID NO: 2, SEQ ID NO: 4, SEQ ID NO: 6, SEQ ID NO: 8, or SEQ ID NO: 10, genes encoding this protein is included as genes according to the present invention as long as this protein can regulate the transcription of genes located downstream of a stress responsive element. The term "several amino acids" preferably refers to 20 or fewer and more preferably 5 or fewer amino acids.

The protein according to the present invention is not limited to a protein comprising an amino acid sequence as shown in SEQ ID NO: 2, SEQ ID NO: 4, SEQ ID NO: 6, SEQ ID NO: 8, or SEQ ID NO: 10. A protein which comprises an amino acid sequence having one or several amino acids deleted, substituted, or added in the amino acid sequence as shown in SEQ ID NO: 2, SEQ ID NO: 4, SEQ ID NO: 6, SEQ ID NO: 8, or SEQ ID NO: 10 is included as a protein according to the present invention as long as it can regulate the transcription of genes located downstream of a stress responsive element. The term "several amino acids" preferably refers to 20 or fewer and more preferably 5 or fewer amino acids.

The introduction of mutation into the gene of the present invention may be performed by conventional techniques such as the Kunkel method, the Gapped duplex method or variations thereof using a mutation introducing kit [e.g. Mutant-K (Takara) or Mutant-G (Takara)] utilizing site-directed mutagenesis or using an LA PCR in vitro Mutagenesis Series Kit (Takara).

Once the nucleotide sequence for the gene of the present invention has been determined, the gene of the present invention can be obtained either by chemical synthesis, by PCR using the cDNA or genomic DNA of the gene as a template, or by the hybridization of a DNA fragment having the above nucleotide sequence as a probe.

2. Analysis of the DRE Binding Ability and Transcription Activating Ability of the Proteins of the Present Invention A. Analysis of the DRE Binding Ability The ability of the protein according to the present invention to bind to DRE can be confirmed by gel shift assay [Urao, T. et al., Plant Cell 5:1529-1539 (1993)] using a fusion protein composed of the protein, GST, and the like. The protein according to the present invention can be prepared by ligating the gene according to the present invention downstream of the glutathione-S-transferase (GST) coding region of a plasmid coding for GST gene (e.g. pGEX-4T-1 vector: Pharmacia) in a manner that the reading frames of the two genes coincide with each other, culturing E. coli that has been transformed with the plasmid under conditions which induce synthesis of the fusion protein, and purifying the protein from the transformed E. coli.

Gel shift assay is a method for examining the interaction between DNA and a protein. A DRE-containing DNA fragment labeled with $^{32}P$ or the like is mixed with the fusion protein described above and incubated, and the resultant mixture is subjected to electrophoresis. After drying, the gel is autoradiographed to detect those bands which have migrated to the back as a result of the binding of the DNA fragment and the protein. The specific binding of the protein according to the present invention to the DRE sequence can be confirmed by showing that the above-mentioned band is not detected when a DNA fragment containing a mutated DRE sequence is used.

B. Analysis of Transcription Activating Ability

The transcription activating ability of the proteins of the present invention can be analyzed by a transactivation experiment using rice protoplast system. For example, OsDREB1A cDNA is ligated to pBI221 plasmid (Clontech) containing CaMV35 S promoter to construct an effector plasmid. On the other hand, the DRE-containing DNA fragment is ligated upstream of TATA promoter located upstream of a β-glucuronidase (GUS) gene to construct a reporter plasmid. Subsequently, these two plasmids are introduced into rice protoplasts and then GUS activity is measured. If GUS activity is increased by the simultaneous expression of OsDREB1A protein, it is understood that OsDREB1A protein expressed in the protoplasts is activating the transcription through the DRE sequence.

In the present invention, preparation of protoplasts and introduction of plasmid DNA into the protoplasts may be performed by the method of Abel et al. [Abel, S. et al., Plant J. 5:421-427 (1994)]. In order to minimize experimental errors resulting from differences in plasmid DNA introduction efficiencies, a plasmid in which luciferase gene is ligated downstream of CaMV35S promoter may be introduced to protoplasts together with the two plasmids described above, thus, β-glucuronidase activity against luciferase activity may be determined. Then, the determined value may be taken to indicate transcription activating ability. β-glucuronidase activity can be determined by the method of Jefferson et al. [Jefferson, R. A. et al., EMBO J. 83:8447-8451 (1986)]; and luciferase activity can be determined using PicaGene Luciferase Assay Kit (Toyo Ink).

3. Preparation of Recombinant Vectors and Transformants

A. Preparation of Recombinant Vectors

The recombinant vector of the present invention can be obtained by ligating (inserting) the gene of the present invention to (into) an appropriate vector. The vector into which the gene of the present invention is to be inserted is not particularly limited as long as it is replicable in a host. For example, plasmid DNA, phage DNA or the like may be used. Plasmid DNA includes plasmids for E. coli hosts such as pBR322, pBR325, pUC118, and pUC119; plasmids for Bacillus subtilis hosts such as pUB110 and pTP5; plasmids for yeast host such as YEp13, YEp24, and YCp50; and plasmids for plant cell host such as pBI221 and pBI121. Phage DNA includes λ phage and the like. Further, animal virus vector such as retrovirus or vaccinia virus; or insect virus vector such as baculovirus may also be used.

In order to insert the gene of the present invention into a vector, for example, a method may be employed in which the purified DNA is cleaved with an appropriate restriction enzyme and then inserted into the restriction site or the multi-cloning site of an appropriate vector DNA for ligation to the vector. The gene of the present invention should be incorporated into the vector in such a manner that the function of the gene is expressed. For this purpose, in addition to a promoter and the gene of the present invention, those containing cis elements such as enhancer, a splicing signal, poly(A) addition signal, selection marker, ribosome binding sequence (SD sequence) or the like can be ligated to the vector of the present invention, if so desired. Examples of selection marker are dihydrofolate reductase gene, ampicillin tolerance gene, neomycin tolerance gene, or the like.

B. Preparation of Transformants

The transformant of the present invention can be obtained by introducing the recombinant vector of the present invention into a host so that the gene of interest can be expressed. The host is not particularly limited as long as the gene of the present invention can be expressed therein. Specific examples of the host include Escherichia bacteria such as E. coli; Bacillus bacteria such as Bacillus subtilis; Pseudomonas bacteria such as Pseudomonas putida; Rhizobium bacteria such as Rhizobium meliloti; yeasts such as Saccharomyces cerevisiae, Schizosaccharomyces pombe; plant cell strains established from Arabidopsis thaliana, tobacco, maize, rice, carrot, etc. or protoplasts prepared from such plants; animal cells such as COS cells, CHO cells; or insect cells such as Sf9 cells and Sf21 cells.

When a bacterium such as E. coli is used as the host, the recombinant vector of the present invention is capable of autonomous replication inside the host and, at the same time, it is preferably composed of a promoter, a ribosome binding sequence, the gene of the present invention, and a transcription termination sequence. The vector may also contain a gene to regulate the promoter. Escherichia coli strains such as HMS174 (DE3), K12, or DH1 may be used. Bacillus subtilis strains such as MI 114 or 207-21 may be used.

Any promoter may be used as long as it is able to direct the expression of the gene of interest in a host such as E. coli. For example, an E. coli- or phage-derived promoter such as trp promoter, lac promoter, $P_L$ promoter, or $P_R$ promoter may be used. An artificially designed and altered promoter such as tac promoter may also be used. Methods for introducing the recombinant vector into a bacterium are not particularly limited, and examples thereof include a method using calcium ions [Cohen, S. N. et al., Proc. Natl. Acad. Sci., USA, 69:2110-2114 (1972)] and electroporation.

When yeast such as *Saccharomyces cerevisiae, Schizosaccharomyces pombe*, or *Pichia pastoris* is used as the host, the promoter is not particularly limited, and any promoter may be used as long as it is able to direct the expression of the gene of interest in yeast. For example, gal1 promoter, gal 10 promoter, heat shock protein promoter, MFα1 promoter, PH05 promoter, PGK promoter, GAP promoter, ADH promoter, or AOX1 promoter can be used.

A method for introducing the recombinant vector into yeast is not particularly limited, and examples thereof include electroporation [Becker, D. M. et al., Methods Enzymol., 194:182-187 (1990)], the spheroplast method [Hinnen, A. et al., Proc. Natl. Acad. Sci., USA, 75:1929-1933 (1978)], and the lithium acetate method [Itoh, H., J. Bacteriol., 153:163-168 (1983)].

When a plant cell is used as the host, for example, cell strains established from rice, maize, wheat, *Arabidopsis thaliana*, tobacco, carrot, etc. or protoplasts prepared from such plants, the promoter to be used is not particularly limited as long as it is able to direct the expression of the gene of interest in plants. Examples thereof include 35S RNA promoter of cauliflower mosaic virus, rd29A gene promoter, and rbcS promoter.

A method for introducing the recombinant vector into a plant includes the method of Abel et al. using polyethylene glycol [Abel, H. et al., Plant J. 5:421-427 (1994)] and electroporation. When an animal cell is used as the host, for example, simian COS-7 or Vero cells, Chinese hamster ovary cells (CHO cells), mouse L cells, rat GH3 cells, human FL cells, or the like, SRα promoter, SV40 promoter, LTR promoter, CMV promoter or the like may be used. The early gene promoter of human cytomegalovirus or the like may also be used.

To introduce the recombinant vector into an animal cell, for example, electroporation, the calcium phosphate method, lipofection, or the like may be used. When an insect cell is used as the host, for example, Sf9 cells, Sf21 cells, or the like, the calcium phosphate method, lipofection, electroporation, or the like may be used.

4. Production of the Proteins According to the Present Invention

The protein of the present invention is a protein having an amino acid sequence encoded by the gene of the present invention; or a protein which has an amino acid sequence having at least one amino acid mutation in the above-described amino acid sequence and is able to regulate the transcription of genes located downstream of a stress responsive element.

The protein of the present invention can be obtained by culturing the transformant in a medium and recovering the protein from the resultant culture product. The term "culture product" means any of the following materials: culture supernatant, cultured cells, cultured microorganisms, or disrupted cells or microorganisms. The transformant of the present invention in a medium is cultured by conventional methods for culturing a host.

As a medium for culturing the transformant obtained from a microorganism host such as *E. coli* or yeast, either a natural or synthetic medium may be used as long as it contains carbon sources, nitrogen sources, and inorganic salts assimilable by the microorganism and is capable of efficient culture of the transformant. When a plant cell is used as the host, vitamins such as thiamine and pyridoxine can be added to the medium, if necessary. When an animal cell is used as the host, serum such as RPMI1640 can be added to the medium, if necessary.

Examples of carbon sources include: carbohydrates such as glucose, fructose, sucrose, and starch; organic acids such as acetic acid and propionic acid; and alcohols such as ethanol and propanol. Examples of nitrogen sources include: ammonia; ammonium salts of inorganic or organic acids such as ammonium chloride, ammonium sulfate, ammonium acetate, and ammonium phosphate; other nitrogen-containing compounds; peptone; meat extract; and corn steep liquor.

Examples of inorganic substances include: monopotassium phosphate, dipotassium phosphate, magnesium phosphate, magnesium sulfate, sodium chloride, iron(I) sulfate, manganese sulfate, copper sulfate, and calcium carbonate. Usually, the culture is carried out under aerobic conditions (such as shaking culture or aeration agitation culture) at approximately 30 to 37° C. for approximately 6 hours to 3 days. During the culture, the pH is maintained at approximately 7.0 to 7.5. The pH is adjusted with an inorganic or organic acid, an alkali solution, or the like.

During the culture, an antibiotic such as ampicillin or tetracycline may be added to the medium, if necessary. When a microorganism transformed with an expression vector containing an inducible promoter is cultured, an inducer may be added to the medium, if necessary. For example, when a microorganism transformed with an expression vector containing Lac promoter is cultured, isopropyl-β-D-thiogalactopyranoside (IPTG) or the like may be added to the medium. When a microorganism transformed with an expression vector containing trp promoter is cultured, indoleacrylic acid (IAA) or the like may be added to the medium.

Usually, the culture is carried out in the presence of 5% $CO_2$ at approximately 30 to 37° C. for approximately 6 hours to 3 days. During the culture, an antibiotic such as kanamycin or penicillin may be added to the medium if necessary. After the culture, the protein of the present invention is extracted by disrupting the cultured microorganism or cell if the protein is produced in the microorganism or cell. If the protein of the present invention is secreted outside of the microorganism or cell, the culture fluid may be used for the following steps as it is or subjected to centrifugation to remove the microorganism or cells. Thereafter, conventional biochemical techniques used for isolating/purifying a protein, for example, ammonium sulfate precipitation, gel chromatography, ion exchange chromatography, and affinity chromatography, are employed independently or in an appropriate combination to isolate and purify the protein of the present invention from the above culture product.

5. Preparation of Transgenic Plants into which the Gene of the Present Invention has been Introduced A transgenic plant tolerant to environmental stresses, in particular, low temperature, freezing, and dehydration stresses, can be produced by introducing DNA encoding the protein of the present invention into a host plant using genetic engineering techniques. A method for introducing the gene of the present invention into a host plant includes indirect introduction such as the *Agrobacterium* infection method and direct introduction such as the particle gun method, polyethylene glycol method, liposome method, and microinjection method. When the *Agrobacterium* infection method is used, the transgenic plant of the present invention can be produced by the following procedure.

A. Preparation of a Recombinant Vector to be Introduced into a Plant and Transformation of *Agrobacterium*

A recombinant vector to be introduced into a plant can be prepared by cleaving with an appropriate restriction enzyme DNA comprising the genes of the present invention, ligating an appropriate linker to the resultant DNA if necessary, and inserting the DNA into a cloning vector for the plant cell host. A binary vector type plasmid such as pBI2113Not, pBI2113, pBI101, pBI121, pGA482, pGAH, and pBIG, or an intermediate vector type plasmid such as pLGV23Neo, pNCAT, and pMON200 may be used as cloning vectors.

When a binary vector type plasmid is used, the gene of interest is inserted between the border sequences (LB, RB) of the binary vector. The resultant recombinant vector is amplified in $E.\ coli$. The amplified recombinant vector is then introduced into $Agrobacterium\ tumefaciens$ C58, LBA4404, EHA101, C58C1Rif$^R$, EHA105, etc. by freeze-thawing, electroporation, or the like. The resultant $Agrobacterium$ is used for the transformation of the plant of interest.

In the present invention, the three-member conjugation method [Nucleic Acids Research, 12:8711 (1984)] may also be used in addition to the method described above to prepare an $Agrobacterium$ containing the gene of the present invention for plant infection. Specifically, plasmid-containing $E.\ coli$ comprising the gene of interest, helper plasmid-containing $E.\ coli$ (e.g. pRK2013), and an $Agrobacterium$ are mixed and cultured on a medium containing rifampicin and kanamycin. Thus, a zygote $Agrobacterium$ for infecting plants can be obtained.

For the expression of a foreign gene and the like in a plant body, a promoter and a terminator for plants should be located upstream and downstream of the structural gene, respectively. Specific examples of promoters which may be utilized in the present invention include cauliflower mosaic virus (CaMV)-derived 35S transcript [Jefferson, R. A. et al., The EMBO J. 6:3901-3907 (1987)]; the promoter for maize ubiquitin gene [Christensen, A. H. et al., Plant Mol. Biol. 18:675-689 (1992)]; the promoter for nopaline synthase (NOS) gene; and the promoter for octopin (OCT) synthase gene. Specific examples of useful terminator include CaMV-derived terminators and NOS-derived terminators. Promoters and terminators are not limited to the above-mentioned as long as they are known to function in plant bodies.

If the promoter used in a transgenic plant is a promoter responsible for the constitutive expression of the gene of interest (e.g., CaMV 35S promoter) and the use thereof has brought about delay in the growth or retardation of the transgenic plant, a promoter which directs transient expression of the gene of interest (e.g., rd29A gene promoter) may be used. If necessary, an intron sequence, which enhances the expression of the gene of the present invention, may be located between the promoter sequence and the gene. For example, the intron from maize alcohol dehydrogenase (Adh1) [Genes & Development 1:1183-1200 (1987)] may be introduced.

In order to efficiently select transformed cells of interest, it is preferable to use an effective selection marker gene in combination with the gene of the present invention. As the selection marker, one or more genes, which are selected from kanamycin tolerance (NPTII) gene, hygromycin phosphotransferase (htp) gene which confers tolerance to the antibiotic hygromycin on plants, phosphinothricin acetyl transferase (bar) gene which confers tolerance to bialaphos, and the like, can be used. The gene of the present invention and the selection marker gene may be incorporated together into a single vector. Alternatively, two types of recombinant DNAs may be used which are incorporated into separate vectors.

B. Introduction of the Gene of the Present Invention into a Host

In the present invention, while the host for the transformant is not particularly limited, it is preferably a plant. The plant may be any cultured plant cells, the entire plant body of a cultured plant, plant organs (such as leaves, petals, stems, roots, rhizomes, or seeds), or plant tissues (such as epidermis, phloem, parenchyma, xylem, or vascular bundle). Plants are preferably monocotyledonous plants such as rice, maize, and wheat. When a cultured plant cell, plant body, plant organ or plant tissue is used as the host, the $Agrobacterium$ infection method, particle gun method, or polyethylene glycol method can be employed to introduce the DNA encoding the protein of the present invention to transform this host plant by introducing a vector into plant sections. Alternatively, a vector can be introduced into a protoplast by electroporation to produce a transformed plant.

For example, when a gene is introduced into $Arabidopsis\ thaliana$ by the $Agrobacterium$ infection method, the step of infecting the plant with an $Agrobacterium$ containing a plasmid comprising the gene of interest is essential. This step can be performed by the vacuum infiltration method [CR Acad. Sci. Paris, Life Science, 316:1194 (1993)]. Specifically, $Arabidopsis\ thaliana$ is grown in a soil composed of equivalent portions of vermiculite and perlite. The $Arabidopsis\ thaliana$ is immersed directly in a culture fluid of an $Agrobacterium$ containing a plasmid comprising the gene of the present invention, placed in a desiccator, and then sucked with a vacuum pump to 65-70 mmHg. Then, the plant is allowed to stand at room temperature for 5-10 min. The plant pot is transferred to a tray, which is covered with a wrap to maintain humidity. On the next day, the wrap is removed. The plant is grown in that state to harvest seeds.

Subsequently, the seeds are sown on MS agar medium supplemented with appropriate antibiotics to select those individuals which have the gene of interest. $Arabidopsis\ thaliana$ grown on this medium are transferred to pots and grown there. As a result, seeds of a transgenic plant into which the gene of the present invention has been introduced can be obtained. Generally, the genes are introduced into the genome of the host plant in a similar manner. However, due to differences in the specific locations on the genome into which the genes have been introduced, the expression of the introduced genes varies. This phenomenon is called "position effect." By assaying transformants with DNA fragments from the introduced gene as a probe by Northern blotting, it is possible to select those transformants in which the introduced gene is expressed more highly.

The confirmation that the gene of interest is integrated in the transgenic plant into which the gene of the present invention has been introduced and in the subsequent generation thereof can be made by extracting DNA from cells and tissues of those plants and detecting the introduced gene by PCR or Southern analysis, which are conventional methods in the art.

C. Analysis of the Expression Level and Expression Site of the Gene of the Present Invention in Plant Issues The expression level and expression site of a gene in a transgenic plant into which the gene of the present invention has been introduced can be analyzed by extracting RNA from cells and tissues of the plant and detecting the mRNA of the introduced gene by RT-PCR or Northern analysis, which are conventional methods in the art. Alternatively, the expression level and expression site can be analyzed directly by Western blotting or the like of the gene product of the present invention using an antibody against the above product.

D. Changes in the mRNA Levels of Various Genes in a Transgenic Plant into which the Gene of the Present Invention has been Introduced It is possible to identify by Northern hybridization those genes whose expression levels are believed to have been changed as a result of the action of the transcription factor of the present invention in a transgenic plant into which the gene of the present invention has been introduced.

For example, plants grown hydroponically or the like are given environmental stress for a specific period of time (e.g. 1 to 2 weeks). Examples of environmental stresses include low temperature, dehydration, and salt stresses. For example, dehydration stress may be given by uprooting the plant from the hydroponic medium and drying it on a filter paper for 10 minutes to 24 hours. Low temperature stress may be given by retaining the plant at 15 to −4° C. for 10 minutes to 24 hours. Salt stress can be given by, for example, replacing the hydroponic solution with a 50 to 500 mM NaCl solution and retaining the plant for 10 minutes to 24 hours.

Total RNAs are respectively prepared from a control plant, which was given no stress, and from the plant, which was given environmental stress, and the resultant total RNAs are subjected to electrophoresis. The expression patterns can be analyzed by Northern hybridization using the probe of the gene to be observed.

E. Evaluation of the Tolerance of the Transgenic Plant to Environmental Stresses The tolerance to environmental stresses of the transgenic plant into which the gene of the present invention has been introduced can be evaluated by setting the transgenic plant in a pot containing a soil comprising vermiculite, perlite and the like, exposing the plant to various environmental stresses, and examining the survival of the plant. Environmental stresses include low temperature, dehydration, and salt stresses. For example, tolerance to dehydration stress can be evaluated by leaving the plant without watering for 2 to 4 weeks and then examining the survival. Tolerance to low temperature and freezing stresses can be evaluated by leaving the plant at 15 to −10° C. for 1 to 10 days, growing it at 20 to 35° C. for 2 days to 3 weeks, and then examining its survival ratio. Tolerance to salt stress can be evaluated by, for example, leaving the plant in 100 to 600 mM NaCl for 1 hour to 7 days, growing it at 20 to 35° C. for 1 to 3 weeks, and then examining its survival rate.

F. Determination of Stress Levels in Plants

The transcription of the gene according to the present invention is activated by low temperature stress, dehydration stress, or salt stress. Therefore, determination of the transcription level of the gene of the present invention enables the assessment of the stress level such as low temperature, dehydration, or salt stress which the plant is subjected to.

The transcription level of the gene according to the present invention can be determined by, for example, RNA gel blot analysis or quantitative PCR. A probe to be used in RNA gel blot analysis can be produced in accordance with any conventional method based on the gene according to the present invention and/or a 100-1000 bp region comprising specific sequence adjacent to the gene. A primer to be used in quantitative PCR can be prepared by any conventional method based on the sequence in the region encoding the gene of the present invention or the region adjacent thereto.

The above-described probe or primer may be used in a kit for determining the transcription level of the gene according to the present invention.

G. Others

In addition, the protein according to the present invention can be utilized by producing an antibody against the protein. The antibody may be a polyclonal or monoclonal antibody. The method for producing an antibody is not particularly limited, and it can be carried out in accordance with any conventional method [see, for example, Sambrook, J et al., Molecular Cloning, Cold Spring Harbor Laboratory Press (1989)]. The antibody can be utilized in, for example, the detection of the protein of interest by Western blotting or immunoprecipitation.

EXAMPLES

The present invention is described in more detail with reference to the following examples, however, the scope of the present invention is not limited to these.

Example 1

Screening of Rice OsDREB Gene

1. Homology Search Against Database

On the basis of the full-length amino acid sequences of DREB1A, DREB1B, DREB1C, DREB2A, and DREB2B genes as shown below, homology search was carried out by BLAST against the database of rice DNA in GenBank.

As a result, four types of genes were discovered: 1 type (OsDREB1B) from EST data, 2 types (OsDREB1C and OsDREB1D) from genome sequence data in terms of the DREB1-homologous gene, and 1 type (OsDREB2A) from EST data in terms of the DREB2-homologous gene.

2. Search of cDNA Library

A. Preparation of cDNA Library

Rice seeds (Nipponbare) were grown hydroponically using distilled water under dark conditions at 25° C. for 15 days. The resulting plant bodies were treated at 4° C. for 2 hours or 24 hours, uprooted from the incubator and dried on a filter paper for 10 hours, or treated with 250 mM NaCl for 10 hours, followed by freezing with liquid nitrogen. Total RNA was extracted from the frozen sample using the guanidine thiocyanate-cesium chloride method, and mRNA was prepared using the Oligo(dt)-cellulose column. cDNA was synthesized using the resultant mRNA as a template and using HybriZAP-2.1 two-hybrid cDNA Gigapack cloning kit (Stratagene) and the cDNA was inserted and cloned in the EcoRI-XhoI cleavage site of HybriZAP-2.1 phagemid vector. This phagemid DNA was packaged using Gigapack III Gold packaging extract (Stratagene). The obtained lambda phage particles containing cDNA were used to infect host *E. coli*, which were then amplified, and these were subsequently recovered. The resulting phage suspension was then stored.

B. Search Using Probe

The sequence containing the ERF/AP2 domain and a conserved region on the N-terminal side of the OsDREB1D genome sequence obtained in (1) was amplified by PCR to produce a probe. The cDNA library, which was prepared in (1), was searched using this probe. As a result, a new DREB1-homologous cDNA (OsDREB1A) was obtained.

The EST clone corresponding to OsDREB1B was provided by the Rice Genome Research Projects. To amplify the full-length of the protein-coding region, OsDREB1C and OsDREB1D were subjected to PCR using a primer that was designed on the basis of predictions from a genome sequence of a transcription initiation site and a termination codon.

The probe for searching the full-length cDNA of OsDREB2A was produced based on the sequence of EST, thereby searching the cDNA library. Since the resultant cDNA clone was predicted to be of an incomplete length, 5'RACE was carried out using DNA prepared from the cDNA library as a template to determine the full-length sequence. Based on this sequence, a primer for amplifying a full-length gene was designed and the full-length gene was obtained by RT-PCR.

C. Nucleotide Sequencing

The nucleotide sequence of the cDNA of the resultant DREB-homologous gene was determined using 377 DNA sequencer (Perkin-Elmer). Further, the ORF was analyzed to determine all the amino acid sequences.

3. Results:

As a result, nucleotide sequences for 5 types of OsDREB genes and corresponding amino acid sequences of OsDREB proteins were identified. As the DREB protein derived from *Arabidopsis thaliana*, all the OsDREB proteins comprised regions which were deduced to be: the ERF/AP2 DNA binding domain at the center, a nuclear localization signal at the N-terminus, and an acidic activation domain at the C-terminus (FIG. 1).

In FIG. 2 and FIG. 3, amino acid sequences of the DREB-homologous proteins from various plants were compared to one another to find highly conserved sequences. Outline letters on colored backgrounds represent highly conserved regions.

Sequence numbers of nucleotide sequences and amino acid sequences of each OsDREB are as follows:
OsDREB1A: nucleotide sequence (SEQ ID NO: 1), amino acid sequence (SEQ ID NO: 2);
OsDREB1B: nucleotide sequence (SEQ ID NO: 3), amino acid sequence (SEQ ID NO: 4);
OsDREB1C: nucleotide sequence (SEQ ID NO: 5), amino acid sequence (SEQ ID NO: 6);
OsDREB1D: nucleotide sequence (SEQ ID NO: 7), amino acid sequence (SEQ ID NO: 8);
OsDREB2A: nucleotide sequence (SEQ ID NO: 9), amino acid sequence (SEQ ID NO: 10).

Example 2

Analysis of Ability of OsDREB Proteins to Bind to DRE

A fusion protein between glutathione-S-transferase (GST) and proteins of OsDREB1A and OsDREB2A was prepared using *E. coli*. The resulting protein was then assessed by gel shift assay to inspect the proteins' binding abilities to DRE.

The 477 bp DNA fragment located from position 69 to position 545 of the nucleotide sequence of OsDREB1A cDNA or the 489 bp DNA fragment located from position 334 to position 822 of the nucleotide sequence of OsDREB2A cDNA was amplified by PCR. Then, the amplified fragment was ligated to the EcoRI-XhoI site of plasmid pGEX-4T-1 (Pharmacia). After the introduction of this plasmid into *E. Coli* XL1-Blue MRF', the *E. coli* was cultured in 500 ml of 2×YT medium (Molecular Cloning (1982), Cold Spring Harbor Laboratory Press). To this culture, 0.1 mM isopropyl β-D-thiogalactoside, which activates the promoter of plasmid pGEX-4T-1, was added to induce the synthesis of a fusion protein of OsDREB1A and GST.

The *E. coli* into which the protein had been induced was suspended in 18 ml of buffer (10 mM Tris-HCl, pH 8.0, 0.1 mM EDTA, 5 mM $MgCl_2$, 400 mM NaCl, 5% glycerol, 0.1 mM phenylmethylsulfonyl fluoride, 0.1 mM dithiothreitol). Then, 1% Triton X-100 and 1 mM EDTA were added thereto. After the cells were disrupted by sonication, the disrupted material was centrifuged at 20,000 g for 1 hour. Then, the protein was purified from the supernatant using glutathione-Sepharose (Pharmacia). The resultant fusion protein was incubated at room temperature for 20 minutes using the DRE sequence-containing 75 bp DNA fragment (SEQ ID NO: 16) labeled with $^{32}P$ as a probe. This mixture was electrophoresed using 5% polyacrylamide containing 0.25×Tris-borate-EDTA at 120 V for 90 minutes. As a result of this gel shift assay, those bands which migrated to the back were detected. When the DNA fragment containing the mutated DRE sequence was used as a probe, such bands were not detected. Thus, it became evident that OsDREB1A and OsDREB2A proteins specifically bind to the DRE sequence (FIG. 4).

Example 3

Preparation of Transformant (Transgenic Plant)

1. Construction of Plant Plasmid
A. Preparation of OsDREB1A Gene Fragment

The 717 bp DNA fragment located from position 69 to position 785 of the nucleotide sequence of cDNA of the OsDREB1A gene was amplified by PCR using the following primers. Thereafter, the amplified fragment was ligated to the BamHI cleavage site of the vector pBluescript SK(–) (Stratagene) to obtain the recombinant plasmid pSKOsDREB1A. This pSKOsDREB1A was cleaved with BamHI to obtain approximately 700 bp DNA fragment containing OsDREB1A gene.

```
Forward:                              (SEQ ID NO: 17)
5'-GGGGATCCATGTGCGGGATCAAGCAGGAGATG-3'

Reverse:                              (SEQ ID NO: 18)
5'-GGGGATCCCTAGTAGCTCCAGAGTGGGAC-3'
```

B. Preparation of pBE2113Not, G-ubi, G35S-ShΔ pBE2113Not (Plant Cell 10: 1391-1406(1998)), G-ubi, and G35S-ShΔ were used as plasmids having promoter DNA. G-ubi and G35S-ShΔ were prepared as follows. At the outset, pBIG plasmid (Nucleic Acids Research 18: 203 (1990)) was cleaved with BamHI, blunt-ended and ligated to delete the BamHI cleavage site. Thereafter the plasmid was cleaved with HindIII and EcoRI. The resultant fragment and an approximately 1.2 kb fragment, which was obtained by cleavage of pBE2113Not plasmid in the same manner, were ligated to each other, thereby preparing pBIG2113Not plasmid.

Subsequently, pBIG2113Not was cleaved with HindIII and BamHI and ligated to a fragment of rd29A promoter (approximately 0.9 kb, Nature Biotechnology 17: 287-291 (1999)), which was cleaved in the same manner, thereby preparing pBIG29APHSNot plasmid. Further, this pBIG29APHSNot plasmid was cleaved with HindIII and SalI and then ligated to a fragment of the ubiquitin gene (Ubi-1) promoter (approximately 2.0 kb, Plant Molecular Biology 18: 675-689 (1992)) of maize, which was cleaved in the same manner, or to a fragment (approximately 1.6 kb, Proceeding National Academy of Science USA 96: 15348-15353 (1999)) containing CaMV 35S promoter of p35S-shΔ-stop and a part of the intron of a sucrose synthase gene (Sh1) of maize. Thus, G-ubi plasmid or G35S-shΔ plasmid was prepared. pBE2113Not, G-ubi, and G35S-shΔ described above were respectively cleaved with BamHI and ligated to the OsDREB1A gene fragment using Ligation High (Toyobo Co., Ltd.). *E. coli* DH5α was transformed using the thus obtained ligation product. After the transformant was cultured, plasmid pBE35S:OsDREB1A, G-ubi: OsDREB1A, and G35S-ShΔ: OsDREB1A were respectively purified therefrom. Subsequently, the nucleotide sequences thereof were determined, and those having OsDREB1A gene bound in the sense direction were selected.

C. Introduction into *Agrobacterium*

The plasmid pBE35S: OsDREB1A-containing *E. coli* DH5α, helper plasmid pRK2013-containing *E. coli* HB101, and *Agrobacterium* C58 were mixed and cultured on LB agar medium at 28° C. for 24 hours. Generated colonies were scraped off and suspended in 1 ml of LB medium. This suspension (10 μl) was coated on LB agar medium containing 100 mg/l rifampicilin and 20 mg/l kanamycin and cultured at 28° C. for 2 days, thereby obtaining zygote *Agrobacterium* C58 (pBE35S: OsDREB1A). By electroporation, the plasmid G-ubi: OsDREB1A and plasmid G35S-ShΔ: OsDREB1A were separately introduced into *Agrobacterium* EHA105, which were then washed with 10% glycerol after culturing. Thus, *Agrobacterium* EHA105 (G-ubi:OsDREB1A) and *Agrobacterium* EHA105 (G35S-shΔ: OsDREB1A) were prepared.

2. Gene Introduction into *Arabidopsis thaliana* by *Agrobacterium* Infection

The zygote was cultured in 10 ml of LB medium containing 100 mg/l rifampicilin and 20 mg/l kanamycin at 28° C. for 24 hours. Subsequently, this culture fluid was added to 500 ml of LB medium and cultured for 24 hours. The resultant culture fluid was centrifuged to remove the medium and suspended in 500 ml of buffer for infection (2.3 g of Murashige and Skoog Plant Salt Mixture (Nihon Pharmaceutical Co., Ltd), 1 ml of Gamborg's vitamin solution, 50 g of sucrose, 200 μl of L-77 (Nippon Unicar Co., Ltd.), and 10 μg of 6-benzylaminopurine, per liter).

On the other hand, 4 to 5 *Arabidopsis thaliana* plant bodies were grown in 9 cm pots containing soil composed of equivalent portions of vermiculite and perlite, for 6 weeks. Then, the *Arabidopsis thaliana* plant body was directly immersed in the *Agrobacterium* suspension of the *Agrobacterium* C58 (pBI35S: OsDREB1A) and placed in a desiccator, which was sucked with a vacuum pump to reduce the pressure to 650 mmHg and then left to stand for 10 min. Subsequently, the plant pot was transferred to a tray and covered with a wrap to maintain humidity. On the next day, the wrap was removed. Thereafter, the plant was grown uncovered to produce seeds. After sterilization in an aqueous solution of sodium hypochlorite, the seeds were sown on an agar medium for selection (MS medium supplemented with 100 mg/l vancomycin and 30 mg/l kanamycin). *Arabidopsis thaliana* grown on this medium were transferred to pots to obtain seeds of the transformed plant.

3. Gene Introduction into Rice by *Agrobacterium* Infection

Rice seeds were immersed in 70% ethanol for 1 minute and sterilized by immersion into 2% sodium hypochlorite for 1 hour. The sterilized seeds were then washed with sterilized water, and 9 grains each of the seeds were sowed onto a plate of N6D solid medium (3.98 g of CHU[$N_6$] Basal Salt Mixture (Sigma), 30 g of sucrose, 100 mg of myo-inositol, 300 mg of casamino acid, 2,878 mg of L-proline, 2 mg of glycine, 0.5 mg of nicotinic acid, 0.5 mg of pyridoxine hydrochloride, 1 mg of thiamine hydrochloride, 2 mg of 2,4-D, and 4 g of Gelrite, per liter, pH 5.8), followed by culturing for 24 days. Thus, callus was induced. The calluses formed from approximately 20 grains of the seeds were transferred to new N6D solid medium, followed by culturing for additional three days.

Separately, *Agrobacterium* EHA105 (G-ubi: OsDREB1A) and *Agrobacterium* EHA105 (G35S-ShD: OsDREB1A) were cultured in 5 ml of YEP medium containing 100 mg/l rifampicilin and 20 mg/l kanamycin (10 g of Bacto peptone, 10 g of Bacto yeast extract, 5 g of NaCl, and 406 mg of $MgCl_2 \cdot 6H_2O$, per liter, pH 7.2) at 28° C. for 24 hours. This *Agrobacterium* was diluted with AAM medium containing 20 mg/l acetosyringon (10 mg of $MnSO_4 \cdot 5H_2O$, 3 mg of $H_3BO_3$, 2 mg of $ZnSO_4 \cdot 7H_2O$, 250 μg of $Na_2MoO_4 \cdot 2H_2O$, 25 μg of $CuSO_4 \cdot 5H_2O$, 25 μg of $CoCl_2 \cdot 6H_2O$, 750 μg of KI, 150 mg of $CaCl_2 \cdot 2H_2O$, 250 mg of $MgSO_4 \cdot 7H_2O$, 40 mg of Fe-EDTA, 150 mg of $NaH_2PO_4 \cdot 2H_2O$, 1 mg of nicotinic acid, 10 mg of thiamine hydrochloride, 1 mg of pyridoxine hydrochloride, 100 mg of myo-inositol, 176.7 mg of L-arginine, 7.5 mg of glycine, 900 mg of L-glutamine, 300 mg of aspartic acid, and 3 g of KCl, per liter, pH 5.2) to bring $O.D._{660}$ to 0.1. Thus, 20 ml of *Agrobacterium* suspension was prepared.

Subsequently, to the callus, which was cultured for 3 days, the *Agrobacterium* suspension was added and then mixed for 1 minute. Thereafter, this callus was placed on a sterilized paper towel to remove excess *Agrobacterium* suspension and then cultured on 2N6-AS solid medium, on which the sterilized filter paper was placed, (3.98 g of CHU[$N_6$] Basal Salt Mixture, 30 g of sucrose, 10 g of glucose, 100 mg of myo-inositol, 300 mg of casamino acid, 2 mg of glycine, 0.5 mg of nicotinic acid, 0.5 mg of pyridoxine hydrochloride, 1 mg of thiamine hydrochloride, 2 mg of 2,4-D, 10 mg of acetosyringon, and 4 g of Gellite, per liter, pH 5.2) at 25° C. for 3 days in the dark. After culturing for 3 days, the culture product was thoroughly washed with an aqueous solution of 3% sucrose containing 500 mg/l carbenicillin until the product did not whiten. The washed culture product was further cultured on N6D solid medium containing 500 mg/l carbenicillin and 10 mg/l hygromycin for 1 week. Thereafter, the resulting culture product was transferred onto a N6D solid medium containing 500 mg/l carbenicillin and 50 mg/l hygromycin and cultured for 18 days. Furthermore, the callus was transferred to a regeneration medium (4.6 g of Murashige and Skoog Plant Salt Mixture (Nihon Pharmaceutical Co., Ltd), 30 g of sucrose, 30 g of sorbitol, 2 g of casamino acid, 100 mg of myo-inositol, 2 mg of glycine, 0.5 mg of nicotinic acid, 0.5 mg of pyridoxine hydrochloride, 0.1 mg of thiamine hydrochloride, 0.2 mg of NAA, 2 mg of kinetin, 250 mg of carbenicillin, 50 mg of hygromycin, and 8 g of agarose, per liter, pH 5.8). The product was transferred to a new medium every week and regeneration. Those having buds grown to approximately 1 cm were transferred to a hormone-free medium (4.6 g of Murashige and Skoog Plant Salt Mixture (Nihon Pharmaceutical Co., Ltd), 30 g of sucrose, 2 mg of glycine, 0.5 mg of nicotinic acid, 0.5 mg of pyridoxine hydrochloride, 0.1 mg of thiamine hydrochloride, 50 mg of hygromycin, and 2.5 g of Gellite, per liter, pH 5.8). Plant bodies, which have grown to approximately 8 cm on the hormone-free medium, were transferred to a pot containing synthetic particulate potting soil (Bonsol No. 1, Sumitomo Chemical Co., Ltd.) to allow the transgenic plant to produce seeds.

Example 4

Analysis of the Transcription Activating Mechanism Using Rice Protoplast

As shown in FIG. 5, to construct an effector plasmid, OsDREB1A cDNA, OsDREB2A cDNA, DREB1A cDNA, and DREB2A cDNA were positioned downstream of the CaMV35S promoter and the intron sequence of sucrose synthetase of maize and ligated to pBI221 plasmid (Clontech). Separately, a reporter plasmid was constructed in which a 75 bp DNA fragment containing DRE of rd-29A promoter was repeatedly inserted twice upstream of the minimal promoter −61 rd29A and a GUS reporter gene.

Subsequently, these two plasmids were introduced into the rice protoplast and GUS activity was then determined based on changes in fluorescence intensity caused by decomposition of 4-methylumbelliferyl-β-D-glucuronide. The fusion gene of CaMV35S promoter-LUC was simultaneously introduced as a standard for the introduction efficiency in each experiment. As a result, OsDREB1A and OsDREB2A genes were found to activate transcription through DRE.

Example 5

Analysis of Expression of OsDREB Gene in Transformant

1. Analysis of Expression of OsDREB Gene in Nontransformant

Expression properties of OsDREB1A, OsDREB1B, OsDREB1C, and OsDREB2A genes in wild-type rice were analyzed by Northern hybridization. Rice was cultured hydroponically at 25° C. under insolation conditions of 16 hours during the day and 8 hours at night for 17 days. Abscisic acid, dehydration, low temperature, salt (NaCl), lesion, and water stresses were separately applied to the plant body. Sampling was accomplished on stress-applied rice every 0, 10, 20, 40, 60 minutes, 2, 5, 10, and 24 hours.

Figure 6:
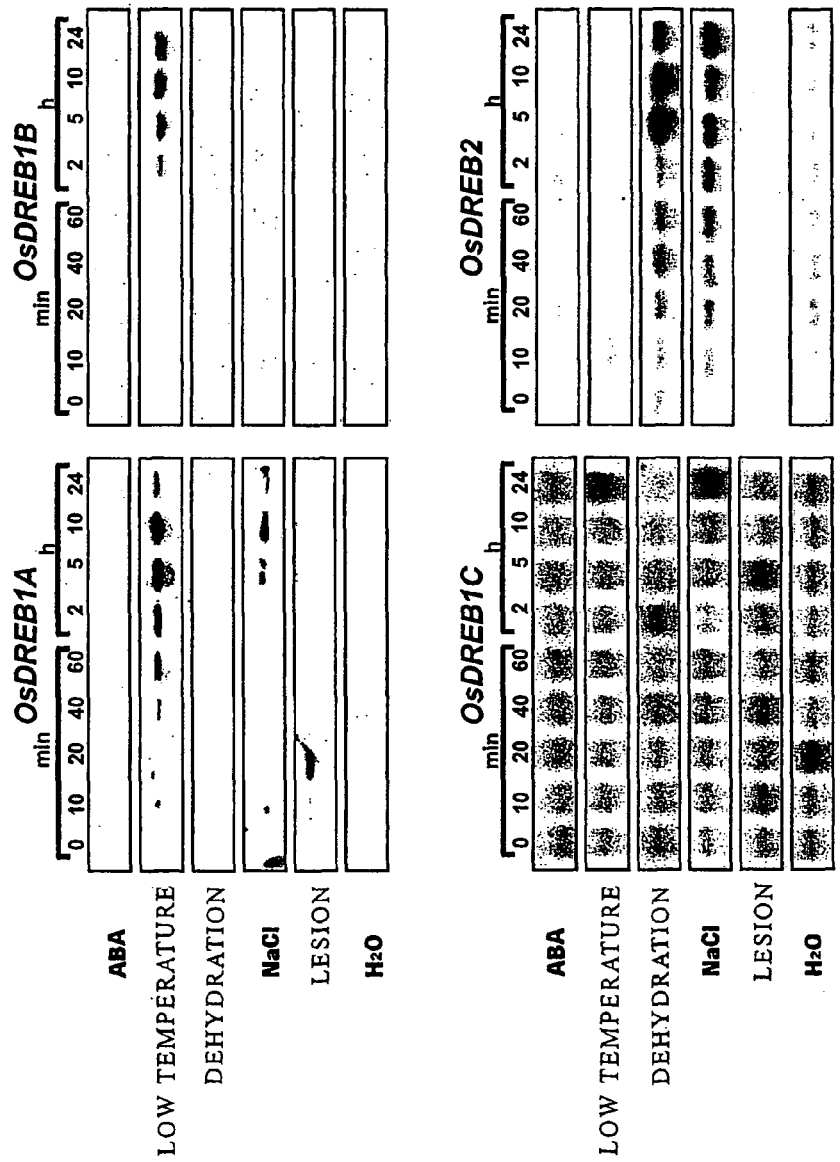
FIG. 6 shows the result of Northern blotting analysis of expression of OsDREB genes.

Each stress was applied to the rice as follows: abscisic acid stress was applied by immersing in a solution containing 100 µM ABA; dehydration stress was applied by drying on a filter paper; low temperature stress was applied by transferring to an incubator which was cooled at 4° C.; salt (NaCl) stress was applied by immersing in an aqueous solution containing 250 mM NaCl; lesion stress was applied by slitting up 8 to 10 cm-high leaves; and water stress was applied by immersing in pure water. Total RNA was separately prepared from a control plant which was given no stress and the plant which was given stress. The RNAs were then subjected to electrophoresis. Thus, the expression of each gene was observed by the Northern method. The result is shown in FIG. 6.

From analysis, the expression of the OsDREB1A gene and that of the OsDREB1B gene were respectively induced mainly by low temperature stress. In contrast, the expression of OsDREB2A was induced mainly by dehydration and salt stresses. Gene expression was constantly observed in OsDREB1C.

2. Analysis of OsDREB Gene Expression in Transformed *Arabidopsis thaliana*

In the same manner as in Example 3, transformants having OsDREB1A, OsDREB1D, and OsDREB2A genes introduced into *Arabidopsis thaliana* were prepared. The mRNA level of the transformant-introduced genes OsDREB1A, OsDREB1D, and OsDREB2A and that of the genes, the expression of which was considered to be altered by the introduced genes, were analyzed by the Northern method. Specifically, partial fragments of rd29A gene, cor15a gene, kin1 gene, and erd10 gene were used as probes (rd29A: SEQ ID NO: 19, cor15a: SEQ ID NO: 20, kin1 SEQ ID NO: 21, erd10: SEQ ID NO: 22), and the mRNA levels were analyzed. In addition to the transformant, transformed *Arabidopsis thaliana* having pBI121 plasmid (Clontech) containing no DREB-homologous gene introduced therein was used as a control to compare the gene expressions.

Approximately 1 g of plant bodies grown on GM agar medium for 3 weeks was exposed to dehydration stress and low temperature stress. Dehydration stress was applied by uprooting the plant from the agar medium and drying it on a petri dish for 5 hours. Low temperature stress was applied by incubating the plant at 4° C. for 5 hours. Total RNA was prepared separately from control plants which are given no stress and plants which were given the dehydration and low temperature stresses. The resultant total RNAs were subjected to electrophoresis. Then, gene expressions were assessed by the Northern method.

Figure 7:
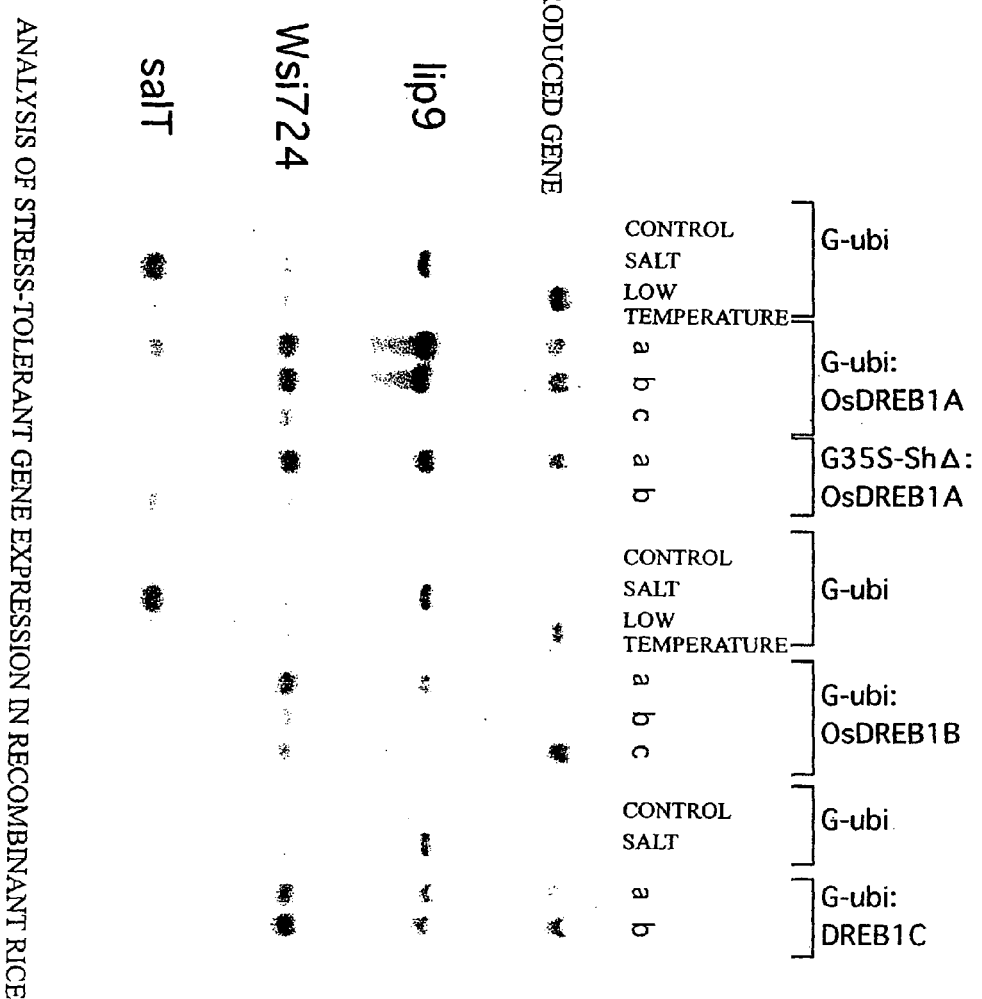
FIG. 7 shows the result of analysis of stress tolerant gene expression in a recombinant *Arabidopsis thaliana*.

Generally, genes are introduced into the genome of a transformant in a similar manner, however, due to differences in the locations on the genome and thereby the expression of the introduced genes vary. This phenomenon is called "position effect." In this experiment, by assaying transformants with DNA fragments from the introduced gene as a probe by the Northern method, those transformants in which the introduced gene was expressed more highly could be selected. Also, by using a DNA fragment of the gene, which could be involved in the stress tolerance, as a probe, OsDREB1A was introduced. Thus, the gene having a varied level of mRNA was identified. The result is shown in FIG. 7.

As a result, the gene having GCCGAC in the promoter was induced more strongly than the gene having ACCGAG In the group of stress tolerant genes of monocotyledonous plants, those having GCCGAC as the DRE sequence exist in a larger amount than those having ACCGAG. Accordingly, it is suggested that, in these monocotyledonous plants, the OsDREB genes allowed the stress tolerant genes to express more efficiently than the DREB genes.

3. Analysis of OsDREB Gene Expression in Transformed Rice

In the same manner as in Example 3, transformants having OsDREB1A, OsDREB1B, and DREB1C genes of *Arabidopsis thaliana* introduced into rice were prepared. The mRNA level of the transformant-introduced genes OsDREB1A, OsDREB1B, and DREB1C of *Arabidopsis thaliana* and that of the gene, the expression of which was considered to be altered by the introduced genes, were analyzed by the Northern method. Specifically, partial fragments of OsDREB1A gene, OsDREB1B gene, DREB1C gene, lip9 gene, Wsi724 gene, and salT gene were used as probes (OsDREB1A: SEQ ID NO: 23, OsDREB1B: SEQ ID NO: 24, DREB1C: SEQ ID NO: 25, lip9: SEQ ID NO: 26, Wsi724: SEQ ID NO: 27, salT: SEQ ID NO: 28), and the expression levels of mRNA were analyzed. In the analysis, in addition to the transformant, transformed rice having G-ubi that contained no DREB-homologous gene introduced therein was used as a control in order to compare gene expressions.

Figure 8:
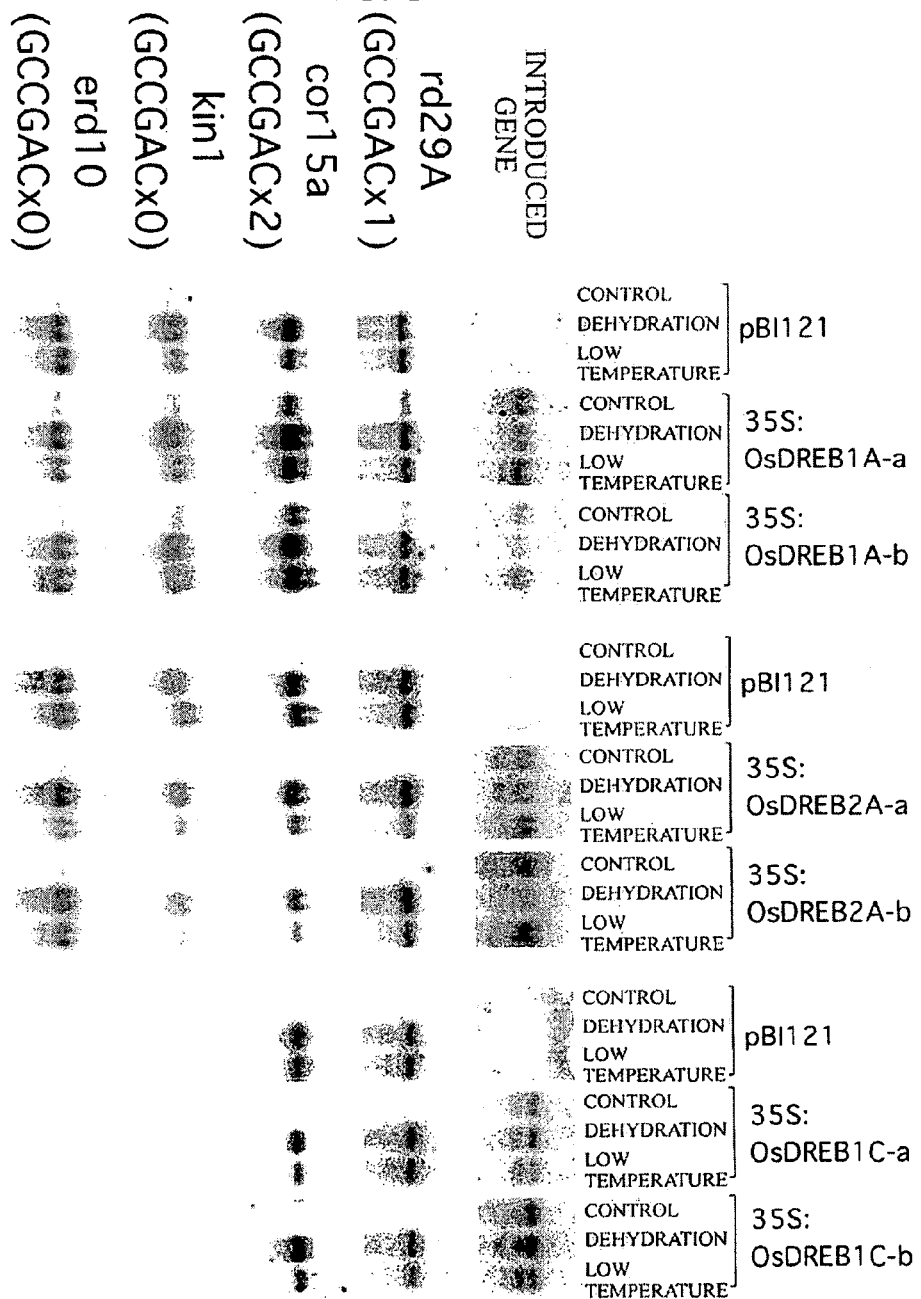
FIG. 8 shows the result of analysis of stress tolerant gene expression in a recombinant rice.

Selection was carried out in a 0.1% Benlate solution containing 30 mg/ml hygromycin for 5 days. Thereafter, the plant was transferred to a pot containing Bonsol No. 1 and was grown for 12 days. Approximately 2 g of the grown plant was subjected to salt (NaCl) and low temperature stresses. Salt stress was applied by uprooting plant body from the soil and immersing in 250 mM NaCl in a test tube for 5 hours. Low temperature stress was applied by incubating the plant body at 4° C. for 5 hours. Total RNAs were separately prepared from a control plant which was given no stress and the plant which was given salt and low temperature stresses, and then subjected to electrophoresis. Thus, the expression of each gene was observed by the Northern method in the same manner as in (2). The result is shown in FIG. 8.

As a result, in the transformed rice having OsDREB1A, OsDREB1B, and DREB1C genes introduced therein, the expression of the lip9 gene having the DRE sequence in the promoter region was induced while the expression of the salT gene having no DRE sequence in the promoter region was not induced. Also, the expression of the Wsi724 gene, the expression of which in the promoter region was not identified but deduced to be a target of OsDREB, based on the expression pattern when stress was applied (dehydration, salt, low temperature inducible, induction by low temperature is slower than that by dehydration and salt), was induced in these transformants.

Example 6

Influences of OsDREB Genes on *Arabidopsis thaliana* Stress Tolerances

In the same manner as in Example 3, transformants having OsDREB1A and DREB1A genes introduced into *Arabidopsis thaliana* were prepared. As a control, *Arabidopsis thaliana*, which was transformed with pBI121 containing no DREB-homologous gene, was prepared. Each tolerance experiment was carried out under following conditions.

1. NaCl Tolerance

NaCl tolerance was inspected as follows. *Arabidopsis thaliana*, which was grown in GM medium for 3 weeks, was immersed in an aqueous solution of 600 mM NaCl for 2 hours, followed by washing. Thereafter, the plant body was transferred into a pot containing Professional potting soil and cultured for 3 weeks, and its survival rate was assessed.

2. Dehydration Tolerance

Dehydration tolerance was investigated as follows. *Arabidopsis thaliana*, which was grown in GM medium for 3 weeks, was transferred in a pot containing soil composed of equivalent portions of vermiculete and perlite, and cultured for 1 week, and water supply was then stopped. After culturing for 2 weeks, its survival ratio was assessed.

3. Freezing Tolerance

Freezing tolerance was investigated as follows. *Arabidopsis thaliana*, which was grown in GM medium for 3 weeks, was transferred into a pot containing Professional potting soil and cultured for 1 week. Thereafter, the plant body was placed at −6° C. for 36 hours and then cultured at 22° C. for 5 days. Its survival ratio was then assessed.

Figure 9:
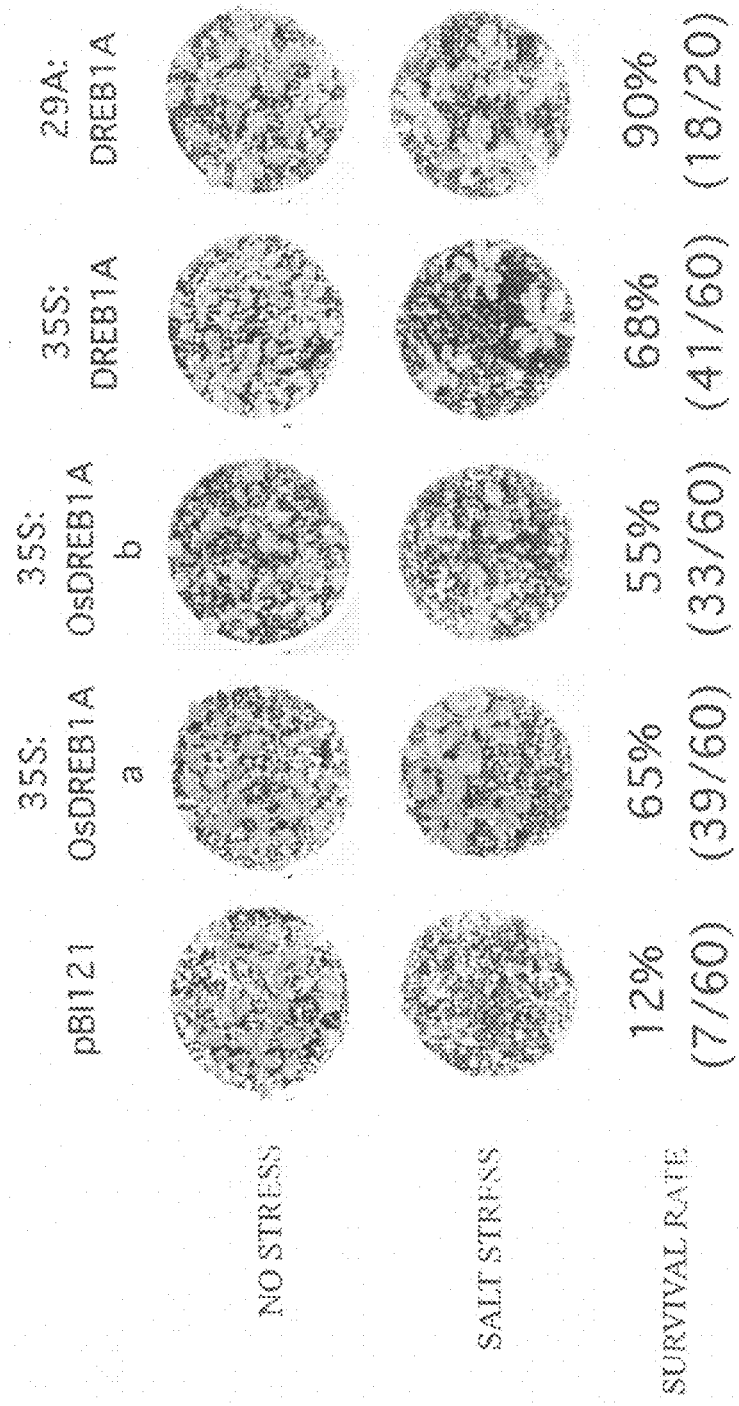
FIG. 9 shows salt stress tolerance of a recombinant plant (*Arabidopsis thaliana*) into which OsDREB1A and DREB1A have been introduced.

In the experiment for inspecting salt stress tolerance, the survival ratio was 12% for the control and 55% or 65% for the OsDREB1A-introduced plant. As for the DREB1A-introduced plant, the survival ratio was 68% for 35S: DREB1A and 90% for 29A: DREB1A. This indicates that the OsDREB genes also improve stress tolerance in dicotyledonous plants (FIG. 9).

All publications, patents and patent applications cited herein are incorporated herein by reference in their entirety.

Free Text of Sequence Listing
SEQ ID NO: 16; probe
SEQ ID NO: 17; primer
SEQ ID NO: 18; primer
SEQ ID NO: 19; probe for rd29a
SEQ ID NO: 20; probe for cor15a
SEQ ID NO: 21; probe for kin1
SEQ ID NO: 22; probe for erd10
SEQ ID NO: 23; probe for OsDREB1A
SEQ ID NO: 24; probe for OsDREB1B
SEQ ID NO: 25; probe for DREB1C
SEQ ID NO: 26; probe for lip9
SEQ ID NO: 27; probe for Wsi724
SEQ ID NO: 28; probe for salT

---

SEQUENCE LISTING

```
<160> NUMBER OF SEQ ID NOS: 28

<210> SEQ ID NO 1
<211> LENGTH: 927
<212> TYPE: DNA
<213> ORGANISM: Oryza sativa
<220> FEATURE:
<221> NAME/KEY: CDS
<222> LOCATION: (69)..(782)

<400> SEQUENCE: 1
cacactcgag cagagcaaat acagttcagg aatcaggagc aagcagaaac acacacacaa      60 atccgaag atg tgc ggg atc aag cag gag atg agc ggc gag tcg tcg ggg     110
         Met Cys Gly Ile Lys Gln Glu Met Ser Gly Glu Ser Ser Gly
           1               5                   10 tcg ccg tgc agc tcg gcg tcg gcg gag cgg cag cac cag acg gtg tgg     158
Ser Pro Cys Ser Ser Ala Ser Ala Glu Arg Gln His Gln Thr Val Trp
 15                  20                  25                  30 acg gcg ccg ccg aag agg ccg gcg ggg cgg acc aag ttc agg gag acg     206
Thr Ala Pro Pro Lys Arg Pro Ala Gly Arg Thr Lys Phe Arg Glu Thr
                 35                  40                  45 agg cac ccg gtg ttc cgc ggc gtg cgg cgg agg ggc aat gcc ggg agg     254
Arg His Pro Val Phe Arg Gly Val Arg Arg Arg Gly Asn Ala Gly Arg
             50                  55                  60 tgg gtg tgc gag gtg cgg gtg ccc ggg cgg cgc ggc tgc agg ctc tgg     302
Trp Val Cys Glu Val Arg Val Pro Gly Arg Arg Gly Cys Arg Leu Trp
         65                  70                  75 ctc ggc acg ttc gac acc gcc gag ggc gcg gcg cgc gcg cac gac gcc     350
Leu Gly Thr Phe Asp Thr Ala Glu Gly Ala Ala Arg Ala His Asp Ala
     80                  85                  90
```

```
gcc atg ctc gcc atc aac gcc ggc ggc ggc ggc ggg gga gca tgc      398
Ala Met Leu Ala Ile Asn Ala Gly Gly Gly Gly Gly Gly Ala Cys
 95             100                 105                 110 tgc ctc aac ttc gcc gac tcc gcg tgg ctc ctc gcc gtg ccg cgc tcc  446
Cys Leu Asn Phe Ala Asp Ser Ala Trp Leu Leu Ala Val Pro Arg Ser
             115                 120                 125 tac cgc acc ctt cgc cga cgt ccg cca cgc cgt gcc gag gcc gtc gag  494
Tyr Arg Thr Leu Arg Arg Arg Pro Pro Arg Arg Ala Glu Ala Val Glu
         130                 135                 140 gac ttc ttc cgg cgc cgc ctc gcc gac gac gcg ctg tcc gcc acg tcg  542
Asp Phe Phe Arg Arg Arg Leu Ala Asp Asp Ala Leu Ser Ala Thr Ser
     145                 150                 155 tcg tcc tcg acg acg ccg tcc acc cca cgc acc gac gac gac gag gag  590
Ser Ser Ser Thr Thr Pro Ser Thr Pro Arg Thr Asp Asp Asp Glu Glu
 160                 165                 170 tcc gcc gcc acc gac ggc gac gag tcc tcc tcc ccg gcc agc gac ctg  638
Ser Ala Ala Thr Asp Gly Asp Glu Ser Ser Ser Pro Ala Ser Asp Leu
175                 180                 185                 190 gcg ttc gaa ctg gac gtc ctg agt gac atg ggc tgg gac ctg tac tac  686
Ala Phe Glu Leu Asp Val Leu Ser Asp Met Gly Trp Asp Leu Tyr Tyr
             195                 200                 205 gcg agc ttg gcg cag ggg atg ctc atg gag cca cca tcg gcg gcg ctc  734
Ala Ser Leu Ala Gln Gly Met Leu Met Glu Pro Pro Ser Ala Ala Leu
         210                 215                 220 ggc gac gac ggt gac gcc atc ctc gcc gac gtc cca ctc tgg agc tac  782
Gly Asp Asp Gly Asp Ala Ile Leu Ala Asp Val Pro Leu Trp Ser Tyr
     225                 230                 235 tagagctcaa tcaactgtac aattttgcct cttttttctc tcttttctgg cttccgatgc  842
caaaattttg gtactgtacg gacactactt tcggtaatgt gatggaacaa gttgcaaaac  902
aaaaaaaaaa aaaaaaaaaa aaaaa                                        927

<210> SEQ ID NO 2
<211> LENGTH: 238
<212> TYPE: PRT
<213> ORGANISM: Oryza sativa

<400> SEQUENCE: 2

Met Cys Gly Ile Lys Gln Glu Met Ser Gly Glu Ser Ser Gly Ser Pro
 1               5                  10                  15

Cys Ser Ser Ala Ser Ala Glu Arg Gln His Gln Thr Val Trp Thr Ala
             20                  25                  30

Pro Pro Lys Arg Pro Ala Gly Arg Thr Lys Phe Arg Glu Thr Arg His
         35                  40                  45

Pro Val Phe Arg Gly Val Arg Arg Gly Asn Ala Gly Arg Trp Val
     50                  55                  60

Cys Glu Val Arg Val Pro Gly Arg Arg Gly Cys Arg Leu Trp Leu Gly
 65                  70                  75                  80

Thr Phe Asp Thr Ala Glu Gly Ala Ala Arg Ala His Asp Ala Ala Met
                 85                  90                  95

Leu Ala Ile Asn Ala Gly Gly Gly Gly Gly Gly Ala Cys Cys Leu
             100                 105                 110

Asn Phe Ala Asp Ser Ala Trp Leu Leu Ala Val Pro Arg Ser Tyr Arg
         115                 120                 125

Thr Leu Arg Arg Arg Pro Pro Arg Arg Ala Glu Ala Val Glu Asp Phe
     130                 135                 140

Phe Arg Arg Arg Leu Ala Asp Asp Ala Leu Ser Ala Thr Ser Ser Ser
```

-continued

```
            145                 150                 155                 160
Ser Thr Thr Pro Ser Thr Pro Arg Thr Asp Asp Glu Glu Ser Ala
                165                 170                 175

Ala Thr Asp Gly Asp Glu Ser Ser Pro Ala Ser Asp Leu Ala Phe
            180                 185                 190

Glu Leu Asp Val Leu Ser Asp Met Gly Trp Asp Leu Tyr Tyr Ala Ser
        195                 200                 205

Leu Ala Gln Gly Met Leu Met Glu Pro Pro Ser Ala Ala Leu Gly Asp
        210                 215                 220

Asp Gly Asp Ala Ile Leu Ala Asp Val Pro Leu Trp Ser Tyr
225                 230                 235

<210> SEQ ID NO 3
<211> LENGTH: 905
<212> TYPE: DNA
<213> ORGANISM: Oryza sativa
<220> FEATURE:
<221> NAME/KEY: CDS
<222> LOCATION: (16)..(669)

<400> SEQUENCE: 3
cagagagagt catcc atg gag gtg gag gag gcg gcg tac agg acg gtg tgg        51
                Met Glu Val Glu Glu Ala Ala Tyr Arg Thr Val Trp
                 1               5                  10 tcg gag ccg ccg aag agg ccg gcg gga agg acc aag ttc agg gag acg         99
Ser Glu Pro Pro Lys Arg Pro Ala Gly Arg Thr Lys Phe Arg Glu Thr
        15                  20                  25 agg cac ccg gtg tac cgc ggc gtg cgg cgg cgc ggg ggg cgg ccg ggc        147
Arg His Pro Val Tyr Arg Gly Val Arg Arg Arg Gly Gly Arg Pro Gly
    30                  35                  40 gcg gcg ggg agg tgg gtg tgc gag gtg cgg gtg ccc ggg gcg cgc ggc        195
Ala Ala Gly Arg Trp Val Cys Glu Val Arg Val Pro Gly Ala Arg Gly
45                  50                  55                  60 tcc agg ctg tgg ctc ggc acg ttc gcc acc gcc gag gcg gcg gcg cgc        243
Ser Arg Leu Trp Leu Gly Thr Phe Ala Thr Ala Glu Ala Ala Ala Arg
                65                  70                  75 gcg cac gac gcc gcc gcg ctg gcg ctc cgc ggc agg gcc gcc tgc ctc        291
Ala His Asp Ala Ala Ala Leu Ala Leu Arg Gly Arg Ala Ala Cys Leu
            80                  85                  90 aac ttc gcc gac tcc gcg tgg cgg atg ccg ccc gtc ccc gcg tcc gcc        339
Asn Phe Ala Asp Ser Ala Trp Arg Met Pro Pro Val Pro Ala Ser Ala
        95                  100                 105 gcg ctc gcc ggc gcg agg ggg gtc agg gac gcc gtc gcc gtg gcc gtc        387
Ala Leu Ala Gly Ala Arg Gly Val Arg Asp Ala Val Ala Val Ala Val
    110                 115                 120 gag gcg ttc cag cgc cag tcg gcc gcg ccg tcg tct ccg gcg gag acc        435
Glu Ala Phe Gln Arg Gln Ser Ala Ala Pro Ser Ser Pro Ala Glu Thr
125                 130                 135                 140 ttc gcc aac gat ggc gac gaa gaa gaa gac aac aag gac gtg ttg ccg        483
Phe Ala Asn Asp Gly Asp Glu Glu Glu Asp Asn Lys Asp Val Leu Pro
                145                 150                 155 gtg gcg gcg gcg gag gtg ttc gac gcg ggg gcg ttc gag ctc gac gac        531
Val Ala Ala Ala Glu Val Phe Asp Ala Gly Ala Phe Glu Leu Asp Asp
            160                 165                 170 ggg ttc agg ttc ggc ggg atg gac gcc ggg tcg tac tac gcg agc ttg        579
Gly Phe Arg Phe Gly Gly Met Asp Ala Gly Ser Tyr Tyr Ala Ser Leu
        175                 180                 185 gcg cag ggg ctg ctc gtc gag ccg ccg gcc gcc gga gcg tgg tgg gag        627
Ala Gln Gly Leu Leu Val Glu Pro Pro Ala Ala Gly Ala Trp Trp Glu
    190                 195                 200
```

```
gac ggc gag ctc gcc ggc tcc gac atg ccg ctc tgg agc tac       669
Asp Gly Glu Leu Ala Gly Ser Asp Met Pro Leu Trp Ser Tyr
205                 210                 215 taatcaaaat ctcgcactga aaagtgtgga caaattttga ttctccagaa attggggggaa    729 aaaagagaac agagtattgg tgaatttaga acagagtagg caatgagact gaggatgaat    789
ggcaattttt gtaattttgg aatgtgccag atttctccct cctttttgtga ttccatctga   849 ttttgaatgt gcagtcaatg aattcctgta aatttacttc tcctctccaa aaaaaa        905

<210> SEQ ID NO 4
<211> LENGTH: 218
<212> TYPE: PRT
<213> ORGANISM: Oryza sativa

<400> SEQUENCE: 4

Met Glu Val Glu Glu Ala Ala Tyr Arg Thr Val Trp Ser Glu Pro Pro
1               5                   10                  15

Lys Arg Pro Ala Gly Arg Thr Lys Phe Arg Glu Thr Arg His Pro Val
                20                  25                  30

Tyr Arg Gly Val Arg Arg Gly Gly Arg Pro Gly Ala Ala Gly Arg
            35                  40                  45

Trp Val Cys Glu Val Arg Val Pro Gly Ala Arg Gly Ser Arg Leu Trp
    50                  55                  60

Leu Gly Thr Phe Ala Thr Ala Glu Ala Ala Ala Arg Ala His Asp Ala
65                  70                  75                  80

Ala Ala Leu Ala Leu Arg Gly Arg Ala Ala Cys Leu Asn Phe Ala Asp
                85                  90                  95

Ser Ala Trp Arg Met Pro Pro Val Pro Ala Ser Ala Ala Leu Ala Gly
            100                 105                 110

Ala Arg Gly Val Arg Asp Ala Val Ala Val Ala Val Glu Ala Phe Gln
        115                 120                 125

Arg Gln Ser Ala Ala Pro Ser Ser Pro Ala Glu Thr Phe Ala Asn Asp
    130                 135                 140

Gly Asp Glu Glu Glu Asp Asn Lys Asp Val Leu Pro Val Ala Ala Ala
145                 150                 155                 160

Glu Val Phe Asp Ala Gly Ala Phe Glu Leu Asp Asp Gly Phe Arg Phe
                165                 170                 175

Gly Gly Met Asp Ala Gly Ser Tyr Tyr Ala Ser Leu Ala Gln Gly Leu
            180                 185                 190

Leu Val Glu Pro Pro Ala Ala Gly Ala Trp Trp Glu Asp Gly Glu Leu
        195                 200                 205

Ala Gly Ser Asp Met Pro Leu Trp Ser Tyr
    210                 215

<210> SEQ ID NO 5
<211> LENGTH: 645
<212> TYPE: DNA
<213> ORGANISM: Oryza sativa
<220> FEATURE:
<221> NAME/KEY: CDS
<222> LOCATION: (1)..(642)

<400> SEQUENCE: 5 atg gag tac tac gag cag gag gag tac gcg acg gtg acg tcg gcg ccg       48
Met Glu Tyr Tyr Glu Gln Glu Glu Tyr Ala Thr Val Thr Ser Ala Pro
1               5                   10                  15 ccg aag cgg ccg gcg ggg agg acc aag ttc agg gag acg agg cac ccg       96
```

```
Pro Lys Arg Pro Ala Gly Arg Thr Lys Phe Arg Glu Thr Arg His Pro
            20                  25                  30 gtg tac cgc ggc gtg cgg cgg cgg ggg ccc gcg ggg cgg tgg gtg tgc        144
Val Tyr Arg Gly Val Arg Arg Arg Gly Pro Ala Gly Arg Trp Val Cys
         35                  40                  45 gag gtc agg gag ccc aac aag aag tcc cgc atc tgg ctc ggc acc ttc        192
Glu Val Arg Glu Pro Asn Lys Lys Ser Arg Ile Trp Leu Gly Thr Phe
 50                  55                  60 gcc acc gcc gag gcc gcc gcg cgc gcc cac gac gtc gcc gcg ctc gcc        240
Ala Thr Ala Glu Ala Ala Ala Arg Ala His Asp Val Ala Ala Leu Ala
 65                  70                  75                  80 ctc cgc ggc cgc ggc gcg tgc ctc aac ttc gcc gac tcg gcc cgc ctc        288
Leu Arg Gly Arg Gly Ala Cys Leu Asn Phe Ala Asp Ser Ala Arg Leu
             85                  90                  95 ctc cgc gtc gac ccg gcc acc ctc gcc acc ccc gac gac atc cgc cgc        336
Leu Arg Val Asp Pro Ala Thr Leu Ala Thr Pro Asp Asp Ile Arg Arg
        100                 105                 110 gcc gcc atc gag ctc gcc gag tca tgc ccg cac gac gcc gcc gcc gcc        384
Ala Ala Ile Glu Leu Ala Glu Ser Cys Pro His Asp Ala Ala Ala Ala
        115                 120                 125 gcc gcc tcc agc tcc gcc gcc gtc gag gcc tcc gcc gcc gcc gcg            432
Ala Ala Ser Ser Ser Ala Ala Val Glu Ala Ser Ala Ala Ala Ala
    130                 135                 140 ccc gcc atg atg atg cag tac cag gac gac atg gcg gcg acg ccg tcc        480
Pro Ala Met Met Met Gln Tyr Gln Asp Asp Met Ala Ala Thr Pro Ser
145                 150                 155                 160 agc tac gac tac gcg tac tac ggc aac atg gac ttc gac cag ccg tcc        528
Ser Tyr Asp Tyr Ala Tyr Tyr Gly Asn Met Asp Phe Asp Gln Pro Ser
                165                 170                 175 tac tac tac gac ggg atg ggc ggc ggc gag tac cag agc tgg cag            576
Tyr Tyr Tyr Asp Gly Met Gly Gly Gly Glu Tyr Gln Ser Trp Gln
            180                 185                 190 atg gac ggc gac gac gat ggt ggc gcc ggc ggc tac ggc ggc ggc gac        624
Met Asp Gly Asp Asp Asp Gly Gly Ala Gly Gly Tyr Gly Gly Gly Asp
        195                 200                 205 gtc aca ctc tgg agc tac tga                                            645
Val Thr Leu Trp Ser Tyr
    210

<210> SEQ ID NO 6
<211> LENGTH: 214
<212> TYPE: PRT
<213> ORGANISM: Oryza sativa

<400> SEQUENCE: 6

Met Glu Tyr Tyr Glu Gln Glu Glu Tyr Ala Thr Val Thr Ser Ala Pro
 1               5                  10                  15

Pro Lys Arg Pro Ala Gly Arg Thr Lys Phe Arg Glu Thr Arg His Pro
            20                  25                  30

Val Tyr Arg Gly Val Arg Arg Arg Gly Pro Ala Gly Arg Trp Val Cys
         35                  40                  45

Glu Val Arg Glu Pro Asn Lys Lys Ser Arg Ile Trp Leu Gly Thr Phe
 50                  55                  60

Ala Thr Ala Glu Ala Ala Ala Arg Ala His Asp Val Ala Ala Leu Ala
 65                  70                  75                  80

Leu Arg Gly Arg Gly Ala Cys Leu Asn Phe Ala Asp Ser Ala Arg Leu
             85                  90                  95

Leu Arg Val Asp Pro Ala Thr Leu Ala Thr Pro Asp Asp Ile Arg Arg
        100                 105                 110
```

```
Ala Ala Ile Glu Leu Ala Glu Ser Cys Pro His Asp Ala Ala Ala
        115                 120                 125

Ala Ala Ser Ser Ala Ala Ala Val Glu Ala Ser Ala Ala Ala Ala
    130                 135                 140

Pro Ala Met Met Met Gln Tyr Gln Asp Asp Met Ala Ala Thr Pro Ser
145                 150                 155                 160

Ser Tyr Asp Tyr Ala Tyr Tyr Gly Asn Met Asp Phe Asp Gln Pro Ser
                165                 170                 175

Tyr Tyr Tyr Asp Gly Met Gly Gly Gly Glu Tyr Gln Ser Trp Gln
            180                 185                 190

Met Asp Gly Asp Asp Asp Gly Gly Ala Gly Gly Tyr Gly Gly Gly Asp
        195                 200                 205

Val Thr Leu Trp Ser Tyr
        210

<210> SEQ ID NO 7
<211> LENGTH: 762
<212> TYPE: DNA
<213> ORGANISM: Oryza sativa
<220> FEATURE:
<221> NAME/KEY: CDS
<222> LOCATION: (1)..(759)

<400> SEQUENCE: 7 atg gag aag aac acc gcc gcc agc ggg caa ttg atg acc tcc tcc gcg      48
Met Glu Lys Asn Thr Ala Ala Ser Gly Gln Leu Met Thr Ser Ser Ala
 1               5                  10                  15 gag gcg acg ccg tcg tcg ccg aag cgg ccg gcg ggg cga acc aag ttc      96
Glu Ala Thr Pro Ser Ser Pro Lys Arg Pro Ala Gly Arg Thr Lys Phe
             20                  25                  30 cag gag acg agg cac cta gtg ttc cgt ggg gtg cga tgg cgt ggg tgc     144
Gln Glu Thr Arg His Leu Val Phe Arg Gly Val Arg Trp Arg Gly Cys
         35                  40                  45 gcg ggg cgg tgg gtg tgc aag gtg cgt gtc ccg ggc agc cgc ggt gac     192
Ala Gly Arg Trp Val Cys Lys Val Arg Val Pro Gly Ser Arg Gly Asp
     50                  55                  60 cgt ttc tgg ata ggc acg tct gac acc gcc gag gag acc gcg cgc acg     240
Arg Phe Trp Ile Gly Thr Ser Asp Thr Ala Glu Glu Thr Ala Arg Thr
 65                  70                  75                  80 cac gac gcc gcc atg ctc gcc ttg tgc ggg gcc tcc gcc agc ctc aac     288
His Asp Ala Ala Met Leu Ala Leu Cys Gly Ala Ser Ala Ser Leu Asn
                 85                  90                  95 ttc gcc gac tct gcc tgg ctg ctc cac gtc ccg cgc gcc ccc gtc gtc     336
Phe Ala Asp Ser Ala Trp Leu Leu His Val Pro Arg Ala Pro Val Val
            100                 105                 110 tcc gga ctc cgg cca cca gct gcc cga tgt gca acg cgc tgc ctg caa     384
Ser Gly Leu Arg Pro Pro Ala Ala Arg Cys Ala Thr Arg Cys Leu Gln
        115                 120                 125 ggc cat cgc cga gtt cca gcg ccg ggc cgg ggg agc acc gcc act gcc     432
Gly His Arg Arg Val Pro Ala Pro Gly Arg Gly Ser Thr Ala Thr Ala
    130                 135                 140 act gcc acc tcc ggc gat gct gca tcg acc gct cct ccg tcg gca ccc     480
Thr Ala Thr Ser Gly Asp Ala Ala Ser Thr Ala Pro Pro Ser Ala Pro
145                 150                 155                 160 gtt ctg tca gcc aaa caa tgc gaa ttc atc ttt ctt tct tca cta gat     528
Val Leu Ser Ala Lys Gln Cys Glu Phe Ile Phe Leu Ser Ser Leu Asp
                165                 170                 175 tgt tgg atg tta atg tca aag ctt atc agc agt agc aga gca aaa gga     576
Cys Trp Met Leu Met Ser Lys Leu Ile Ser Ser Ser Arg Ala Lys Gly
```

```
                       180                 185                 190
tcg ttg tgc ctg cga aaa aat ccc att tca ttt tgc atg gtt aca aat       624
Ser Leu Cys Leu Arg Lys Asn Pro Ile Ser Phe Cys Met Val Thr Asn
        195                 200                 205 tct tac act gct ctt ttg ctc gaa tac att ata ttg cag atg aat tca       672
Ser Tyr Thr Ala Leu Leu Leu Glu Tyr Ile Ile Leu Gln Met Asn Ser
    210                 215                 220 atg atc gtt tta atc cac gaa tta tca aaa tat caa gtc ttt ctg cta      720
Met Ile Val Leu Ile His Glu Leu Ser Lys Tyr Gln Val Phe Leu Leu
225                 230                 235                 240 cta acc atg ata aca cac cac ctt ttt caa tgg agg agg tag              762
Leu Thr Met Ile Thr His His Leu Phe Gln Trp Arg Arg
                245                 250

<210> SEQ ID NO 8
<211> LENGTH: 253
<212> TYPE: PRT
<213> ORGANISM: Oryza sativa

<400> SEQUENCE: 8

Met Glu Lys Asn Thr Ala Ala Ser Gly Gln Leu Met Thr Ser Ser Ala
 1               5                  10                  15

Glu Ala Thr Pro Ser Pro Lys Arg Pro Ala Gly Arg Thr Lys Phe
             20                  25                  30

Gln Glu Thr Arg His Leu Val Phe Arg Gly Val Arg Trp Arg Gly Cys
         35                  40                  45

Ala Gly Arg Trp Val Cys Lys Val Arg Val Pro Gly Ser Arg Gly Asp
     50                  55                  60

Arg Phe Trp Ile Gly Thr Ser Asp Thr Ala Glu Glu Thr Ala Arg Thr
 65                  70                  75                  80

His Asp Ala Ala Met Leu Ala Leu Cys Gly Ala Ser Ala Ser Leu Asn
                 85                  90                  95

Phe Ala Asp Ser Ala Trp Leu Leu His Val Pro Arg Ala Pro Val Val
            100                 105                 110

Ser Gly Leu Arg Pro Pro Ala Ala Arg Cys Ala Thr Arg Cys Leu Gln
        115                 120                 125

Gly His Arg Arg Val Pro Ala Pro Gly Arg Gly Ser Thr Ala Thr Ala
    130                 135                 140

Thr Ala Thr Ser Gly Asp Ala Ala Ser Thr Ala Pro Pro Ser Ala Pro
145                 150                 155                 160

Val Leu Ser Ala Lys Gln Cys Glu Phe Ile Phe Leu Ser Ser Leu Asp
                165                 170                 175

Cys Trp Met Leu Met Ser Lys Leu Ile Ser Ser Arg Ala Lys Gly
            180                 185                 190

Ser Leu Cys Leu Arg Lys Asn Pro Ile Ser Phe Cys Met Val Thr Asn
        195                 200                 205

Ser Tyr Thr Ala Leu Leu Leu Glu Tyr Ile Ile Leu Gln Met Asn Ser
    210                 215                 220

Met Ile Val Leu Ile His Glu Leu Ser Lys Tyr Gln Val Phe Leu Leu
225                 230                 235                 240

Leu Thr Met Ile Thr His His Leu Phe Gln Trp Arg Arg
                245                 250

<210> SEQ ID NO 9
<211> LENGTH: 1393
<212> TYPE: DNA
<213> ORGANISM: Oryza sativa
```

```
<220> FEATURE:
<221> NAME/KEY: CDS
<222> LOCATION: (334)..(1155)

<400> SEQUENCE: 9
gctggatgag ccagcagccg ccccgcccg cggttgcttc ccctcccac cacgtcaaaa      60 cccaacccca accatgatgc tcctgcgcca ccaccaccac ccccacagcg gcgccgccac     120
caccagcagc agctgcagcg gcggcggcgg ctgttagaga ggagggcaca caccaccacc     180
gacaccgaca cgctcgccat gccaccaagc gaggcggcgg cgtgaggcga cgcagatctg     240 aacgaggag gaataggaag aagggaggag gaggggaggg agaggagttg aaagagttgg      300
aggaggagga gatctctttc ttgttcccgc tcg atg gag cgg ggg gag ggg agg     354
                                     Met Glu Arg Gly Glu Gly Arg
                                       1               5 agg gga gat tgc tcc gtg caa gtg agg aag aag aga acg cga agg aaa     402
Arg Gly Asp Cys Ser Val Gln Val Arg Lys Lys Arg Thr Arg Arg Lys
        10                  15                  20 agc gat ggc cct gat tca atc gct gaa acc atc aag tgg tgg aag gag     450
Ser Asp Gly Pro Asp Ser Ile Ala Glu Thr Ile Lys Trp Trp Lys Glu
 25                  30                  35 caa aac cag aag ctc cag gag gag aat agc tcc agg aaa gcg cca gcc     498
Gln Asn Gln Lys Leu Gln Glu Glu Asn Ser Ser Arg Lys Ala Pro Ala
 40                  45                  50                  55 aag ggg tcc aag aaa ggg tgc atg gct ggg aaa gga ggt ccg gaa aat     546
Lys Gly Ser Lys Lys Gly Cys Met Ala Gly Lys Gly Gly Pro Glu Asn
             60                  65                  70 tca aat tgt gct tac cgc ggt gtc agg caa cgg aca tgg ggt aag tgg     594
Ser Asn Cys Ala Tyr Arg Gly Val Arg Gln Arg Thr Trp Gly Lys Trp
         75                  80                  85 gtg gct gag atc cgt gaa cca aac cgt gga agg cgc cta tgg cta gga     642
Val Ala Glu Ile Arg Glu Pro Asn Arg Gly Arg Arg Leu Trp Leu Gly
     90                  95                 100 tca ttt cct act gcg ctg gag gct gcg cat gca tac gat gag gcg gca     690
Ser Phe Pro Thr Ala Leu Glu Ala Ala His Ala Tyr Asp Glu Ala Ala
105                 110                 115 agg gca atg tat ggt ccc aca gca cgt gtc aat ttt gca gat aat tcc     738
Arg Ala Met Tyr Gly Pro Thr Ala Arg Val Asn Phe Ala Asp Asn Ser
120                 125                 130                 135 aca gat gcc aac tct ggc tgc aca tca gca cct tca ttg atg atg tct     786
Thr Asp Ala Asn Ser Gly Cys Thr Ser Ala Pro Ser Leu Met Met Ser
             140                 145                 150 aat ggg ccg gcc act ata cct tct gat gag aag gat gag ctg gaa tct     834
Asn Gly Pro Ala Thr Ile Pro Ser Asp Glu Lys Asp Glu Leu Glu Ser
         155                 160                 165 cct cct ttc atc gtg gct aat ggg cca gct gtg ttg tat cag cct gat     882
Pro Pro Phe Ile Val Ala Asn Gly Pro Ala Val Leu Tyr Gln Pro Asp
     170                 175                 180 aag aag gat gtg ttg gaa cgt gta gtc cct gag gtg cag gat gtt aaa     930
Lys Lys Asp Val Leu Glu Arg Val Val Pro Glu Val Gln Asp Val Lys
185                 190                 195 aca gaa ggg agc aat ggc ttg aaa cgt gtt tgt cag gag cgg aag aat     978
Thr Glu Gly Ser Asn Gly Leu Lys Arg Val Cys Gln Glu Arg Lys Asn
200                 205                 210                 215 atg gag gta tgt gaa tca gaa ggg atc gtt tta cac aaa gaa gtg aac    1026
Met Glu Val Cys Glu Ser Glu Gly Ile Val Leu His Lys Glu Val Asn
             220                 225                 230 ata agt tat gat tat ttc aat gtc cat gaa gtt gtt gag atg ata att    1074
Ile Ser Tyr Asp Tyr Phe Asn Val His Glu Val Val Glu Met Ile Ile
         235                 240                 245
```

```
gtt gaa tta agt gct gat cag aaa acg gaa gta cat gaa gag tac caa    1122
Val Glu Leu Ser Ala Asp Gln Lys Thr Glu Val His Glu Glu Tyr Gln
        250                 255                 260 gag gga gat gat ggg ttt agc ctt ttc tcc tat tagagtagta gtcatgctgc   1175
Glu Gly Asp Asp Gly Phe Ser Leu Phe Ser Tyr
265                 270 gggtcaatag gaatatttca ttctagctgc taggggatac ttcaaatatc tgcaacctga   1235
agctttgtag tcatttacgg ttttcgtctt actgggtaat agctttatat atactataag   1295
ccaactggta caagaagttg tactgtgtgt tgagtgcact gtggtaaaaa tgaatctata   1355
tttaatgagc ttactctgtc aaaaaaaaaa aaaaaaa                            1393

<210> SEQ ID NO 10
<211> LENGTH: 274
<212> TYPE: PRT
<213> ORGANISM: Oryza sativa

<400> SEQUENCE: 10

Met Glu Arg Gly Glu Gly Arg Gly Asp Cys Ser Val Gln Val Arg
1               5                   10                  15

Lys Lys Arg Thr Arg Arg Lys Ser Asp Gly Pro Asp Ser Ile Ala Glu
                20                  25                  30

Thr Ile Lys Trp Trp Lys Glu Gln Asn Gln Lys Leu Gln Glu Glu Asn
            35                  40                  45

Ser Ser Arg Lys Ala Pro Ala Lys Gly Ser Lys Lys Gly Cys Met Ala
        50                  55                  60

Gly Lys Gly Gly Pro Glu Asn Ser Asn Cys Ala Tyr Arg Gly Val Arg
65                  70                  75                  80

Gln Arg Thr Trp Gly Lys Trp Val Ala Glu Ile Arg Glu Pro Asn Arg
                85                  90                  95

Gly Arg Arg Leu Trp Leu Gly Ser Phe Pro Thr Ala Leu Glu Ala Ala
            100                 105                 110

His Ala Tyr Asp Glu Ala Ala Arg Ala Met Tyr Gly Pro Thr Ala Arg
        115                 120                 125

Val Asn Phe Ala Asp Asn Ser Thr Asp Ala Asn Ser Gly Cys Thr Ser
    130                 135                 140

Ala Pro Ser Leu Met Met Ser Asn Gly Pro Ala Thr Ile Pro Ser Asp
145                 150                 155                 160

Glu Lys Asp Glu Leu Glu Ser Pro Pro Phe Ile Val Ala Asn Gly Pro
                165                 170                 175

Ala Val Leu Tyr Gln Pro Asp Lys Lys Asp Val Leu Glu Arg Val Val
            180                 185                 190

Pro Glu Val Gln Asp Val Lys Thr Glu Gly Ser Asn Gly Leu Lys Arg
        195                 200                 205

Val Cys Gln Glu Arg Lys Asn Met Glu Val Cys Glu Ser Glu Gly Ile
    210                 215                 220

Val Leu His Lys Glu Val Asn Ile Ser Tyr Asp Tyr Phe Asn Val His
225                 230                 235                 240

Glu Val Val Glu Met Ile Ile Val Glu Leu Ser Ala Asp Gln Lys Thr
                245                 250                 255

Glu Val His Glu Glu Tyr Gln Glu Gly Asp Asp Gly Phe Ser Leu Phe
            260                 265                 270

Ser Tyr
```

<210> SEQ ID NO 11
<211> LENGTH: 933
<212> TYPE: DNA
<213> ORGANISM: Arabidopsis thaliana
<220> FEATURE:
<221> NAME/KEY: CDS
<222> LOCATION: (119)..(766)

<400> SEQUENCE: 11

```
cctgaactag aacagaaaga gagagaaact attatttcag caaaccatac caacaaaaaa      60
gacagagatc ttttagttac cttatccagt ttcttgaaac agagtactct tctgatca       118 atg aac tca ttt tct gct ttt tct gaa atg ttt ggc tcc gat tac gag      166
Met Asn Ser Phe Ser Ala Phe Ser Glu Met Phe Gly Ser Asp Tyr Glu
 1               5                  10                  15 tct tcg gtt tcc tca ggc ggt gat tat att ccg acg ctt gcg agc agc      214
Ser Ser Val Ser Ser Gly Gly Asp Tyr Ile Pro Thr Leu Ala Ser Ser
             20                  25                  30 tgc ccc aag aaa ccg gcg ggt cgt aag aag ttt cgt gag act cgt cac      262
Cys Pro Lys Lys Pro Ala Gly Arg Lys Lys Phe Arg Glu Thr Arg His
         35                  40                  45 cca ata tac aga gga gtt cgt cgg aga aac tcc ggt aag tgg gtt tgt      310
Pro Ile Tyr Arg Gly Val Arg Arg Arg Asn Ser Gly Lys Trp Val Cys
     50                  55                  60 gag gtt aga gaa cca aac aag aaa aca agg att tgg ctc gga aca ttt      358
Glu Val Arg Glu Pro Asn Lys Lys Thr Arg Ile Trp Leu Gly Thr Phe
 65                  70                  75                  80 caa acc gct gag atg gca gct cga gct cac gac gtt gcc gct tta gcc      406
Gln Thr Ala Glu Met Ala Ala Arg Ala His Asp Val Ala Ala Leu Ala
                 85                  90                  95 ctt cgt ggc cga tca gcc tgt ctc aat ttc gct gac tcg gct tgg aga      454
Leu Arg Gly Arg Ser Ala Cys Leu Asn Phe Ala Asp Ser Ala Trp Arg
            100                 105                 110 ctc cga atc ccg gaa tca act tgc gct aag gac atc caa aag gcg gcg      502
Leu Arg Ile Pro Glu Ser Thr Cys Ala Lys Asp Ile Gln Lys Ala Ala
        115                 120                 125 gct gaa gct gcg ttg gcg ttt cag gat gag atg tgt gat gcg acg acg      550
Ala Glu Ala Ala Leu Ala Phe Gln Asp Glu Met Cys Asp Ala Thr Thr
    130                 135                 140 gat cat ggc ttc gac atg gag gag acg ttg gtg gag gct att tac acg      598
Asp His Gly Phe Asp Met Glu Glu Thr Leu Val Glu Ala Ile Tyr Thr
145                 150                 155                 160 gcg gaa cag agc gaa aat gcg ttt tat atg cac gat gag gcg atg ttt      646
Ala Glu Gln Ser Glu Asn Ala Phe Tyr Met His Asp Glu Ala Met Phe
                165                 170                 175 gag atg ccg agt ttg ttg gct aat atg gca gaa ggg atg ctt ttg ccg      694
Glu Met Pro Ser Leu Leu Ala Asn Met Ala Glu Gly Met Leu Leu Pro
            180                 185                 190 ctt ccg tcc gta cag tgg aat cat aat cat gaa gtc gac ggc gat gat      742
Leu Pro Ser Val Gln Trp Asn His Asn His Glu Val Asp Gly Asp Asp
        195                 200                 205 gac gac gta tcg tta tgg agt tat taaaactcag attattattt ccatttttag      796
Asp Asp Val Ser Leu Trp Ser Tyr
    210                 215 tacgatactt tttatttttat tattattttt agatcctttt ttagaatgga atcttcatta      856
tgtttgtaaa actgagaaac gagtgtaaat taaattgatt cagtttcagt ataaaaaaaa      916
aaaaaaaaaa aaaaaaa                                                     933
```

<210> SEQ ID NO 12
<211> LENGTH: 1437

<210> TYPE: DNA
<213> ORGANISM: Arabidopsis thaliana
<220> FEATURE:
<221> NAME/KEY: CDS
<222> LOCATION: (167)..(1171)

<400> SEQUENCE: 12

```
gctgtctgat aaaagaaga ggaaaactcg aaaaagctac acacaagaag aagaagaaaa      60
gatacgagca agaagactaa acacgaaagc gatttatcaa ctcgaaggaa gagactttga    120
ttttcaaatt tcgtcccta tagattgtgt tgtttctggg aaggag atg gca gtt        175
                                                  Met Ala Val
                                                    1 tat gat cag agt gga gat aga aac aga aca caa att gat aca tcg agg      223
Tyr Asp Gln Ser Gly Asp Arg Asn Arg Thr Gln Ile Asp Thr Ser Arg
  5                  10                  15 aaa agg aaa tct aga agt aga ggt gac ggt act act gtg gct gag aga      271
Lys Arg Lys Ser Arg Ser Arg Gly Asp Gly Thr Thr Val Ala Glu Arg
 20                  25                  30                  35 tta aag aga tgg aaa gag tat aac gag acc gta gaa gaa gtt tct acc      319
Leu Lys Arg Trp Lys Glu Tyr Asn Glu Thr Val Glu Glu Val Ser Thr
                 40                  45                  50 aag aag agg aaa gta cct gcg aaa ggg tcg aag aag ggt tgt atg aaa      367
Lys Lys Arg Lys Val Pro Ala Lys Gly Ser Lys Lys Gly Cys Met Lys
 55                  60                  65 ggt aaa gga gga cca gag aat agc cga tgt agt ttc aga gga gtt agg      415
Gly Lys Gly Gly Pro Glu Asn Ser Arg Cys Ser Phe Arg Gly Val Arg
 70                  75                  80 caa agg att tgg ggt aaa tgg gtt gct gag atc aga gag cct aat cga      463
Gln Arg Ile Trp Gly Lys Trp Val Ala Glu Ile Arg Glu Pro Asn Arg
 85                  90                  95 ggt agc agg ctt tgg ctt ggt act ttc cct act gct caa gaa gct gct      511
Gly Ser Arg Leu Trp Leu Gly Thr Phe Pro Thr Ala Gln Glu Ala Ala
100                 105                 110                 115 tct gct tat gat gag gct gct aaa gct atg tat ggt cct ttg gct cgt      559
Ser Ala Tyr Asp Glu Ala Ala Lys Ala Met Tyr Gly Pro Leu Ala Arg
                120                 125                 130 ctt aat ttc cct cgg tct gat gcg tct gag gtt acg agt acc tca agt      607
Leu Asn Phe Pro Arg Ser Asp Ala Ser Glu Val Thr Ser Thr Ser Ser
            135                 140                 145 cag tct gag gtg tgt act gtt gag act cct ggt tgt gtt cat gtg aaa      655
Gln Ser Glu Val Cys Thr Val Glu Thr Pro Gly Cys Val His Val Lys
        150                 155                 160 aca gag gat cca gat tgt gaa tct aaa ccc ttc tcc ggt gga gtg gag      703
Thr Glu Asp Pro Asp Cys Glu Ser Lys Pro Phe Ser Gly Gly Val Glu
165                 170                 175 ccg atg tat tgt ctg gag aat ggt gcg gaa gag atg aag aga ggt gtt      751
Pro Met Tyr Cys Leu Glu Asn Gly Ala Glu Glu Met Lys Arg Gly Val
180                 185                 190                 195 aaa gcg gat aag cat tgg ctg agc gag ttt gaa cat aac tat tgg agt      799
Lys Ala Asp Lys His Trp Leu Ser Glu Phe Glu His Asn Tyr Trp Ser
                200                 205                 210 gat att ctg aaa gag aaa gag aaa cag aag gag caa ggg att gta gaa      847
Asp Ile Leu Lys Glu Lys Glu Lys Gln Lys Glu Gln Gly Ile Val Glu
            215                 220                 225 acc tgt cag caa caa cag cag gat tcg cta tct gtt gca gac tat ggt      895
Thr Cys Gln Gln Gln Gln Gln Asp Ser Leu Ser Val Ala Asp Tyr Gly
        230                 235                 240 tgg ccc aat gat gtg gat cag agt cac ttg gat tct tca gac atg ttt      943
Trp Pro Asn Asp Val Asp Gln Ser His Leu Asp Ser Ser Asp Met Phe
245                 250                 255
```

-continued

```
gat gtc gat gag ctt cta cgt gac cta aat ggc gac gat gtg ttt gca    991
Asp Val Asp Glu Leu Leu Arg Asp Leu Asn Gly Asp Asp Val Phe Ala
260             265                 270                 275 ggc tta aat cag gac cgg tac ccg ggg aac agt gtt gcc aac ggt tca   1039
Gly Leu Asn Gln Asp Arg Tyr Pro Gly Asn Ser Val Ala Asn Gly Ser
            280                 285                 290 tac agg ccc gag agt caa caa agt ggt ttt gat ccg cta caa agc ctc   1087
Tyr Arg Pro Glu Ser Gln Gln Ser Gly Phe Asp Pro Leu Gln Ser Leu
    295                 300                 305 aac tac gga ata cct ccg ttt cag ctc gag gga aag gat ggt aat gga   1135
Asn Tyr Gly Ile Pro Pro Phe Gln Leu Glu Gly Lys Asp Gly Asn Gly
310                 315                 320 ttc ttc gac gac ttg agt tac ttg gat ctg gag aac taaacaaaac        1181
Phe Phe Asp Asp Leu Ser Tyr Leu Asp Leu Glu Asn
325                 330                 335 aatatgaagc tttttggatt tgatatttgc cttaatccca caacgactgt tgattctcta  1241
tccgagtttt agtgatatag agaactacag aacacgtttt ttcttgttat aaaggtgaac  1301
tgtatatatc gaaacagtga tatgacaata gagaagacaa ctatagtttg ttagtctgct  1361
tctcttaagt tgttctttag atatgtttta tgttttgtaa aacaggaat gaataataca   1421 cacttgtaaa aaaaa                                                   1437

<210> SEQ ID NO 13
<211> LENGTH: 937
<212> TYPE: DNA
<213> ORGANISM: Arabidopsis thaliana
<220> FEATURE:
<221> NAME/KEY: CDS
<222> LOCATION: (164)..(802)

<400> SEQUENCE: 13
cttgaaaaag aatctacctg aaagaaaaa aagagagag agatataaat agctttacca     60
agacagatat actatctttt attaatccaa aaagactgag aactctagta actacgtact  120
acttaaacct tatccagttt cttgaaacag agtactctga tca atg aac tca ttt    175
                                                Met Asn Ser Phe
                                                1 tca gct ttt tct gaa atg ttt ggc tcc gat tac gag cct caa ggc gga   223
Ser Ala Phe Ser Glu Met Phe Gly Ser Asp Tyr Glu Pro Gln Gly Gly
5                   10                  15                  20 gat tat tgt ccg acg ttg gcc acg agt tgt ccg aag aaa ccg gcg ggc   271
Asp Tyr Cys Pro Thr Leu Ala Thr Ser Cys Pro Lys Lys Pro Ala Gly
                25                  30                  35 cgt aag aag ttt cgt gag act cgt cac cca att tac aga gga gtt cgt   319
Arg Lys Lys Phe Arg Glu Thr Arg His Pro Ile Tyr Arg Gly Val Arg
            40                  45                  50 caa aga aac tcc ggt aag tgg gtt tct gaa gtg aga gag cca aac aag   367
Gln Arg Asn Ser Gly Lys Trp Val Ser Glu Val Arg Glu Pro Asn Lys
    55                  60                  65 aaa acc agg att tgg ctc ggg act ttc caa acc gct gag atg gca gct   415
Lys Thr Arg Ile Trp Leu Gly Thr Phe Gln Thr Ala Glu Met Ala Ala
70                  75                  80 cgt gct cac gac gtc gct gca tta gcc ctc cgt ggc cga tca gca tgt   463
Arg Ala His Asp Val Ala Ala Leu Ala Leu Arg Gly Arg Ser Ala Cys
85                  90                  95                  100 ctc aac ttc gct gac tcg gct tgg cgg cta cga atc ccg gag tca aca   511
Leu Asn Phe Ala Asp Ser Ala Trp Arg Leu Arg Ile Pro Glu Ser Thr
            105                 110                 115 tgc gcc aag gat atc caa aaa gcg gct gct gaa gcg gcg ttg gct ttt   559
Cys Ala Lys Asp Ile Gln Lys Ala Ala Ala Glu Ala Ala Leu Ala Phe
```

```
Cys Ala Lys Asp Ile Gln Lys Ala Ala Ala Glu Ala Ala Leu Ala Phe
            120                 125                 130 caa gat gag acg tgt gat acg acg acc acg aat cat ggc ctg gac atg        607
Gln Asp Glu Thr Cys Asp Thr Thr Thr Thr Asn His Gly Leu Asp Met
            135                 140                 145 gag gag acg atg gtg gaa gct att tat aca ccg gaa cag agc gaa ggt        655
Glu Glu Thr Met Val Glu Ala Ile Tyr Thr Pro Glu Gln Ser Glu Gly
150                 155                 160 gcg ttt tat atg gat gag gag aca atg ttt ggg atg ccg act ttg ttg        703
Ala Phe Tyr Met Asp Glu Glu Thr Met Phe Gly Met Pro Thr Leu Leu
165                 170                 175                 180 gat aat atg gct gaa ggc atg ctt tta ccg ccg ccg tct gtt caa tgg        751
Asp Asn Met Ala Glu Gly Met Leu Leu Pro Pro Pro Ser Val Gln Trp
            185                 190                 195 aat cat aat tat gac ggc gaa gga gat ggt gac gtg tcg ctt tgg agt        799
Asn His Asn Tyr Asp Gly Glu Gly Asp Gly Asp Val Ser Leu Trp Ser
            200                 205                 210 tac taatattcga tagtcgtttc cattttgta ctatagtttg aaaatattct              852
Tyr agttccttt tttagaatgg ttccttcatt ttatttatt ttattgttgt agaaacgagt        912 ggaaataat tcaatacaaa aaaaa                                             937

<210> SEQ ID NO 14
<211> LENGTH: 944
<212> TYPE: DNA
<213> ORGANISM: Arabidopsis thaliana
<220> FEATURE:
<221> NAME/KEY: CDS
<222> LOCATION: (135)..(782)

<400> SEQUENCE: 14
cctgaattag aaaagaaaga tagatagaga aataaatatt ttatcatacc atacaaaaaa       60
agacagagat cttctactta ctctactctc ataaacctta tccagtttct tgaaacagag      120
tactcttctg atca atg aac tca ttt tct gcc ttt tct gaa atg ttt ggc        170
                 Met Asn Ser Phe Ser Ala Phe Ser Glu Met Phe Gly
                 1               5                   10 tcc gat tac gag tct ccg gtt tcc tca ggc ggt gat tac agt ccg aag        218
Ser Asp Tyr Glu Ser Pro Val Ser Ser Gly Gly Asp Tyr Ser Pro Lys
            15                  20                  25 ctt gcc acg agc tgc ccc aag aaa cca gcg gga agg aag aag ttt cgt        266
Leu Ala Thr Ser Cys Pro Lys Lys Pro Ala Gly Arg Lys Lys Phe Arg
    30                  35                  40 gag act cgt cac cca att tac aga gga gtt cgt caa aga aac tcc ggt        314
Glu Thr Arg His Pro Ile Tyr Arg Gly Val Arg Gln Arg Asn Ser Gly
45                  50                  55                  60 aag tgg gtg tgt gag ttg aga gag cca aac aag aaa acg agg att tgg        362
Lys Trp Val Cys Glu Leu Arg Glu Pro Asn Lys Lys Thr Arg Ile Trp
                65                  70                  75 ctc ggg act ttc caa acc gct gag atg gca gct cgt gct cac gac gtc        410
Leu Gly Thr Phe Gln Thr Ala Glu Met Ala Ala Arg Ala His Asp Val
            80                  85                  90 gcc gcc ata gct ctc cgt ggc aga tct gcc tgt ctc aat ttc gct gac        458
Ala Ala Ile Ala Leu Arg Gly Arg Ser Ala Cys Leu Asn Phe Ala Asp
        95                  100                 105 tcg gct tgg cgg cta cga atc ccg gaa tca acc tgt gcc aag gaa atc        506
Ser Ala Trp Arg Leu Arg Ile Pro Glu Ser Thr Cys Ala Lys Glu Ile
    110                 115                 120 caa aag gcg gcg gct gaa gcc gcg ttg aat ttt caa gat gag atg tgt        554
Gln Lys Ala Ala Ala Glu Ala Ala Leu Asn Phe Gln Asp Glu Met Cys
```

```
                                                                       -continued
            125                 130                 135                 140
cat atg acg acg gat gct cat ggt ctt gac atg gag gag acc ttg gtg         602
His Met Thr Thr Asp Ala His Gly Leu Asp Met Glu Glu Thr Leu Val
                        145                 150                 155 gag gct att tat acg ccg gaa cag agc caa gat gcg ttt tat atg gat         650
Glu Ala Ile Tyr Thr Pro Glu Gln Ser Gln Asp Ala Phe Tyr Met Asp
                160                 165                 170 gaa gag gcg atg ttg ggg atg tct agt ttg ttg gat aac atg gcc gaa         698
Glu Glu Ala Met Leu Gly Met Ser Ser Leu Leu Asp Asn Met Ala Glu
            175                 180                 185 ggg atg ctt tta ccg tcg ccg tcg gtt caa tgg aac tat aat ttt gat         746
Gly Met Leu Leu Pro Ser Pro Ser Val Gln Trp Asn Tyr Asn Phe Asp
        190                 195                 200 gtc gag gga gat gat gac gtg tcc tta tgg agc tat taaaattcga              792
Val Glu Gly Asp Asp Asp Val Ser Leu Trp Ser Tyr
205                 210                 215 tttttatttc catttttggt attatagctt tttatacatt tgatcctttt ttagaatgga       852
tcttcttctt tttttggttg tgagaaacga atgtaaatgg taaaagttgt tgtcaaatgc       912
aaatgttttt gagtgcagaa tatataatct tt                                     944

<210> SEQ ID NO 15
<211> LENGTH: 1420
<212> TYPE: DNA
<213> ORGANISM: Arabidopsis thaliana
<220> FEATURE:
<221> NAME/KEY: CDS
<222> LOCATION: (183)..(1172)

<400> SEQUENCE: 15
gagacgctag aaagaacgcg aaagcttgcg aagaagattt gcttttgatc gacttaacac        60
gaacaacaaa caacatctgc gtgataaaga agagattttt gcctaaataa agaagagatt       120
cgactctaat cctggagtta tcattcacga tagattctta gattgcgact ataaagaaga      180 ag atg gct gta tat gaa caa acc gga acc gag cag ccg aag aaa agg          227
   Met Ala Val Tyr Glu Gln Thr Gly Thr Glu Gln Pro Lys Lys Arg
   1               5                   10                  15 aaa tct agg gct cga gca ggt ggt tta acg gtg gct gat agg cta aag         275
Lys Ser Arg Ala Arg Ala Gly Gly Leu Thr Val Ala Asp Arg Leu Lys
                20                  25                  30 aag tgg aaa gag tac aac gag att gtt gaa gct tcg gct gtt aaa gaa         323
Lys Trp Lys Glu Tyr Asn Glu Ile Val Glu Ala Ser Ala Val Lys Glu
            35                  40                  45 gga gag aaa ccg aaa cgc aaa gtt cct gcg aaa ggg tcg aag aaa ggt         371
Gly Glu Lys Pro Lys Arg Lys Val Pro Ala Lys Gly Ser Lys Lys Gly
        50                  55                  60 tgt atg aag ggt aaa gga gga cca gat aat tct cac tgt agt ttt aga         419
Cys Met Lys Gly Lys Gly Gly Pro Asp Asn Ser His Cys Ser Phe Arg
65                  70                  75 gga gtt aga caa agg att tgg ggt aaa tgg gtt gca gag att cga gaa         467
Gly Val Arg Gln Arg Ile Trp Gly Lys Trp Val Ala Glu Ile Arg Glu
    80                  85                  90                  95 ccg aaa ata gga act aga ctt tgg ctt ggt act ttt cct acc gcg gaa         515
Pro Lys Ile Gly Thr Arg Leu Trp Leu Gly Thr Phe Pro Thr Ala Glu
                100                 105                 110 aaa gct gct tcc gct tat gat gaa gcg gct acc gct atg tac ggt tca         563
Lys Ala Ala Ser Ala Tyr Asp Glu Ala Ala Thr Ala Met Tyr Gly Ser
            115                 120                 125 ttg gct cgt ctt aac ttc cct cag tct gtt ggg tct gag ttt act agt         611
Leu Ala Arg Leu Asn Phe Pro Gln Ser Val Gly Ser Glu Phe Thr Ser
```

```
              130                 135                 140
acg tct agt caa tct gag gtg tgt acg gtt gaa aat aag gcg gtt gtt       659
Thr Ser Ser Gln Ser Glu Val Cys Thr Val Glu Asn Lys Ala Val Val
            145                 150                 155 tgt ggt gat gtt tgt gtg aag cat gaa gat act gat tgt gaa tct aat       707
Cys Gly Asp Val Cys Val Lys His Glu Asp Thr Asp Cys Glu Ser Asn
160                 165                 170                 175 cca ttt agt cag att tta gat gtt aga gaa gag tct tgt gga acc agg       755
Pro Phe Ser Gln Ile Leu Asp Val Arg Glu Glu Ser Cys Gly Thr Arg
                180                 185                 190 ccg gac agt tgc acg gtt gga cat caa gat atg aat tct tcg ctg aat       803
Pro Asp Ser Cys Thr Val Gly His Gln Asp Met Asn Ser Ser Leu Asn
            195                 200                 205 tac gat ttg ctg tta gag ttt gag cag cag tat tgg ggc caa gtt ttg       851
Tyr Asp Leu Leu Leu Glu Phe Glu Gln Gln Tyr Trp Gly Gln Val Leu
        210                 215                 220 cag gag aaa gag aaa ccg aag cag gaa gaa gag ata cag caa cag            899
Gln Glu Lys Glu Lys Pro Lys Gln Glu Glu Glu Ile Gln Gln Gln
    225                 230                 235 caa cag gaa cag caa cag caa cag ctg caa ccg gat ttg ctt act gtt       947
Gln Gln Glu Gln Gln Gln Gln Gln Leu Gln Pro Asp Leu Leu Thr Val
240                 245                 250                 255 gca gat tac ggt tgg cct tgg tct aat gat att gta aat gat cag act       995
Ala Asp Tyr Gly Trp Pro Trp Ser Asn Asp Ile Val Asn Asp Gln Thr
                260                 265                 270 tct tgg gat cct aat gag tgc ttt gat att aat gaa ctc ctt gga gat      1043
Ser Trp Asp Pro Asn Glu Cys Phe Asp Ile Asn Glu Leu Leu Gly Asp
            275                 280                 285 ttg aat gaa cct ggt ccc cat cag agc caa gac caa aac cac gta aat      1091
Leu Asn Glu Pro Gly Pro His Gln Ser Gln Asp Gln Asn His Val Asn
        290                 295                 300 tct ggt agt tat gat ttg cat ccg ctt cat ctc gag cca cac gat ggt      1139
Ser Gly Ser Tyr Asp Leu His Pro Leu His Leu Glu Pro His Asp Gly
305                 310                 315 cac gag ttc aat ggt ttg agt tct ctg gat att tgagagttct gaggcaatgg    1192
His Glu Phe Asn Gly Leu Ser Ser Leu Asp Ile
320                 325                 330 tcctacaaga ctacaacata atctttggat tgatcatagg agaaacaaga aataggtgtt    1252
aatgatctga ttcacaatga aaaatatttt aataactcta tagtttttgt tctttccttg    1312
gatcatgaac tgttgcttct catctattga gttaatatag cgaatagcag agtttctctc    1372
tttcttctct ttgtagaaaa aaaaaaaaaa aaaaaaaaaa aaaaaaaa                 1420

<210> SEQ ID NO 16
<211> LENGTH: 75
<212> TYPE: DNA
<213> ORGANISM: Artificial Sequence
<220> FEATURE:
<223> OTHER INFORMATION: Description of Artificial Sequence:probe

<400> SEQUENCE: 16
acatcagttt gaaagaaaag ggaaaaaaag aaaaaataaa taaagatat actaccgaca        60 tgagttccaa aaagc                                                        75

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence:primer
```

<400> SEQUENCE: 17
ggggatccat gtgcgggatc aagcaggaga tg                                32

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 18
ggggatcccT agtagctcca gagtgggac                                    29

<210> SEQ ID NO 19
<211> LENGTH: 281
<212> TYPE: DNA
<213> ORGANISM: Artificial Sequence
<220> FEATURE:
<223> OTHER INFORMATION: Description of Artificial Sequence:probe for
      rd29a gene

<400> SEQUENCE: 19
gatctctacc gagaaggcag catcggagga gggtgaggcg gtggaagagg aagtgaaagg    60
aggaggagga atggttggga ggattaaagg atggttcggt ggtggtgcga ctgatgaggt   120
gaagccagaa tcgccacatt ctgttgaaga ggctccaaaa tcatctggct ggtttggtgg   180
tggtgcgacg gaggaggtga agccaaaatc gcctcattcc gttgaagagt ctccacaatc   240
acttggctcc actgttgttc cggtgcagaa ggagctttaa g                      281

<210> SEQ ID NO 20
<211> LENGTH: 690
<212> TYPE: DNA
<213> ORGANISM: Artificial Sequence
<220> FEATURE:
<223> OTHER INFORMATION: Description of Artificial Sequence:probe for
      cor15a gene

<400> SEQUENCE: 20
aaaaactcct cctttcattt ccaaacaaaa acttcttttt attctcacat cttaaagatc    60
tctctcatgg cgatgtcttt ctcaggagct gttctcactg gtatggcttc ttctttccac   120
agcggagcca agcagagcag cttcggcgct gtcagagtca gccagaaaac tcagttcgtc   180
gtcgtttctc aacgcaagaa gtcgttgatc tacgccgcta aggtgacgg caacatcctc    240 gatgacctca acgaggccac aaagaaagct tcagatttcg tgacggataa acaaaagag    300 gcattagcag atggtgagaa agcgaaagac tacgttgttg aaaaaaacag tgaaaccgca   360
gatacattgg gtaaagaagc tgagaaagct gcggcgtatg tggaggagaa aggaaaagaa   420
gccgcaaaca aggcggcaga gttcgcggag ggtaaagcag gagaggctaa ggatgccaca   480
aagtaggatc ttacctaatc agttaatttc aagcacttaa actcgtagat atattgatcc   540
atatcctctc tcttcatgtt taatagtact tacaataaga tgagtccgtt gtaatttcta   600
ttaatttcac atcgcaactg aaataagata tggtatccac agtcaccgtc acattcttta   660
atgttttgca aaatattcaa tagacaaatt                                   690

<210> SEQ ID NO 21
<211> LENGTH: 301
<212> TYPE: DNA
<213> ORGANISM: Artificial Sequence
<220> FEATURE:

-continued

```
<223> OTHER INFORMATION: Description of Artificial Sequence:probe for
      kin1 gene

<400> SEQUENCE: 21
atcatcacta accaaaacac acttcaaaaa cgattttaca agaaataaat atctgaaaaa      60
atgtcagaga ccaacaagaa tgccttccaa gccggtcaga ccgctggcaa agctgaggag    120
aagagcaatg ttctgctgga caaggccaag gatgctgcag ctggtgctgg agctggagca    180
caacaggcgg gaaagagtgt atcggatgcg gcagcgggag gtgttaactt cgtgaaggac    240
aagaccggcc tgaacaagta gcgattcggg tcaaatttgg gagttataat ttcccttttc    300
t                                                                    301

<210> SEQ ID NO 22
<211> LENGTH: 1024
<212> TYPE: DNA
<213> ORGANISM: Artificial Sequence
<220> FEATURE:
<223> OTHER INFORMATION: Description of Artificial Sequence:probe for
      erd10 gene

<400> SEQUENCE: 22
ctcaaagctc aaatcgaaat ttctagtttc tctttatcat tcacgctaag tgttcaatcg      60
aatcaagatt aagtatggca gaagagtaca agaacaccgt tccagagcag gagaccccta    120
aggttgcaac agaggaatca tcggcgccag agattaagga gcggggaatg ttcgatttct    180
tgaagaaaaa ggaggaagtt aaacctcaag aaacgacgac tctcgcgtct gagtttgagc    240
acaagactca gatctctgaa ccagagtcgt tgtggccaa gcacgaagaa gaggaacata    300
agcctactct tctcgagcag cttcaccaga agcacgagga ggaagaagaa aacaagccaa    360
gtctcctcga caaactccac cgatccaaca gctcttcttc ctcttcgagt gatgaagaag    420
gtgaagacgg tgagaagaag aagaaggaga aaaagaagaa gattgttgaa ggagatcatg    480
tgaaaacagt ggaagaagag aatcaaggag taatggacag gattaaggag aagtttccac    540
tcggagagaa accaggggt gatgatgtac cagtcgtcac caccatgcca gcaccacatt    600
cggtagagga tcacaaacca gaggaagaag agaagaaagg gtttatggat aagatcaagg    660
agaagcttcc aggccacagc aagaaaccag aggattcaca agtcgtcaac accacaccgc    720
tggttgaaac agcaacaccg attgctgaca tcccggagga gaagaaggga tttatggaca    780
agatcaaaga gaagcttcca ggttatcacg ccaagaccac tggagaggaa gagaagaaag    840
aaaaagtgtc tgattaagag aaaaatatga taagagtgaa taataatgat gtgggagtgg    900
gacttatgtt gtttttttgtt ttttgttgat cattgtctct tttattttgt ctttctagct    960
gttctccaag tttgtgttta gagttagatc atttgtgtct aaaatctata aaattatttt   1020
atct                                                                1024

<210> SEQ ID NO 23
<211> LENGTH: 359
<212> TYPE: DNA
<213> ORGANISM: Artificial Sequence
<220> FEATURE:
<223> OTHER INFORMATION: Description of Artificial Sequence:probe for
      OsDREB1A gene

<400> SEQUENCE: 23
ctcctcgccg tgccgcgctc ctaccgcacc ctcgccgacg tccgccacgc cgtcgccgag      60
gccgtcgagg acttcttccg gcgccgcctc gccgacgacg cgctgtccgc cacgtcgtcg    120
```

-continued

```
tcctcgacga cgccgtccac cccacgcacc gacgacgacg aggagtccgc cgccaccgac    180
ggcgacgagt cctcctcccc ggccagcgac ctggcgttcg aactggacgt cctgagtgac    240
atgggctggg acctgtacta cgcgagcttg gcgcagggga tgctcatgga gccaccatcg    300
gcggcgctcg cgacgacgg tgacgccatc ctcgccgacg tcccactctg agctacta      359
```

<210> SEQ ID NO 24
<211> LENGTH: 389
<212> TYPE: DNA
<213> ORGANISM: Artificial Sequence
<220> FEATURE:
<223> OTHER INFORMATION: Description of Artificial Sequence:probe for
      OsDREB1B gene

<400> SEQUENCE: 24

```
cttgcctcaa cttcgccgac ttcgcgtggc ggatgccgcc cgtccccgcg tccgccgcgc     60
tcgccggcgc gagggggtc agggacgccg tcgccgtggc cgtcgaggcg ttccagcgcc    120
agtcggccgc gccgtcgtct ccggcggaga ccttcgccaa cgatggcgac gaagaagaag    180
acaacaagga cgtgttgccg gtggcggcgg cggaggtgtt cgacgcgggg gcgttcgagc    240
tcgacgacgg gttcaggttc ggcgggatgg acgccgggtc gtactacgcg agcttggcgc    300
aggggctgct cgtcgagccg ccggccgccg agcgtggtg ggaggacggc gagctcgccg    360
gctccgacat gccgctctgg agctactaa                                    389
```

<210> SEQ ID NO 25
<211> LENGTH: 944
<212> TYPE: DNA
<213> ORGANISM: Artificial Sequence
<220> FEATURE:
<223> OTHER INFORMATION: Description of Artificial Sequence:probe for
      DREB1C gene

<400> SEQUENCE: 25

```
cctgaattag aaaagaaaga tagatagaga aataaatatt ttatcatacc atacaaaaaa     60
agacagagat cttctactta ctctactctc ataaacctta tccagttct tgaaacagag    120 tactcttctg atcaatgaac tcattttctg ccttttctga aatgtttggc tccgattacg    180
agtctccggt ttcctcaggc ggtgattaca gtccgaagct tgccacgagc tgccccaaga    240
aaccagcggg aaggaagaag tttcgtgaga ctcgtcaccc aatttacaga ggagttcgtc    300
aaagaaactc cggtaagtgg gtgtgtgagt tgagagagcc aaacaagaaa acgaggattt    360
ggctcgggac tttccaaacc gctgagatgg cagctcgtgc tcacgacgtc gccgccatag    420
ctctccgtgg cagatctgcc tgtctcaatt tcgctgactc ggcttggcgg ctacgaatcc    480
cggaatcaac ctgtgccaag gaaatccaaa aggcggcggc tgaagccgcg ttgaattttc    540
aagatgagat gtgtcatatg acgacggatg ctcatggtct tgacatggag agaccttgg    600 tggaggctat ttatacgccg gaacagagcc aagatgcgtt tatatggat gaagaggcga    660 tgttggggat gtctagtttg ttggataaca tggccgaagg gatgcttta ccgtcgccgt    720 cggttcaatg gaactataat tttgatgtcg agggagatga tgacgtgtcc ttatggagct    780
attaaaattc gatttttatt tccattttg gtattatagc tttttataca tttgatcctt    840
ttttagaatg gatcttcttc ttttttggt tgtgagaaac gaatgtaaat ggtaaaagtt    900
gttgtcaaat gcaaatgttt ttgagtgcag aatatataat cttt                   944
```

<210> SEQ ID NO 26
<211> LENGTH: 720

<210> SEQ ID NO 26
<211> LENGTH: 720
<212> TYPE: DNA
<213> ORGANISM: Artificial Sequence
<220> FEATURE:
<223> OTHER INFORMATION: Description of Artificial Sequence:probe for lip9 gene

<400> SEQUENCE: 26

```
agagctcgtc acagctcaaa caagtcaaga gcgaatagtt cttgctgatc tgttgtttga      60
ttactttagt tctcgagagg ctttagctga atccatcgat cgatcatgga ggatgagagg     120
aacacggaga gccaccaggg tggcgaggct gcagagcagg tggaggtgaa ggacaggggc     180
ctcttcgaca acctccttgg caggaagaag gacgatcagc cggaggagaa gaagcatgag     240
gaggagcttg tcaccggcat ggagaaggtc tccgtggaag agccaaagaa ggaggagcac     300
cacgccgagg gcgagaagaa ggagagcctc ctctccaagc tgcaccgatc cagctccagc     360
tccagctcgt cgagtgatga ggaagaggag gtgatcgatg acaacggcga ggtggtcaag     420
aggaagaaga agaaggggct caaggagaag atcaaggaga agctgcccgg ccacaaggac     480
catgccggtg agcatgctcc tccgcccgcg gcgacgggct tccgcgccg gctccgctgc     540
atccgtggtg acggccgcgc ccacgccanc tcctgctccc gtggtgactc acggcgatca     600
ccaccacgac acccgccgtc cccgtggana agatcgagg gtgatcacgc cnagacggag     660
gcgaccctgc cacgtgcccc cgaggaggan aanaagggc tttctcgaca agatcaagga     720
```

<210> SEQ ID NO 27
<211> LENGTH: 353
<212> TYPE: DNA
<213> ORGANISM: Artificial Sequence
<220> FEATURE:
<223> OTHER INFORMATION: Description of Artificial Sequence:probe for Wsi724 gene

<400> SEQUENCE: 27

```
gctagcagag tagcaatcca ttccgatcca tcaaatttct cttgagaccg tagagagaga      60
gagaggcgcc aaccatggcc ggcatcatcc acaagatcga ggagaagctc cacatgggcg     120
gaggcgagca caagaaggaa gacgagcaca agaaggaggg ggagcaccac aagaaggacg     180
gggagcacaa ggaaggcgtg gtggagaaga tcaaggacaa gatcaccggc gaccacggcg     240
acggcggcga gcacaaggag aagaaggaca agaagaagaa gaaggagaag aagcacggcg     300
aggagggcca ccaccacgac ggccacagca gcagcagcag cgacagcgac tgg           353
```

<210> SEQ ID NO 28
<211> LENGTH: 413
<212> TYPE: DNA
<213> ORGANISM: Artificial Sequence
<220> FEATURE:
<223> OTHER INFORMATION: Description of Artificial Sequence:probe for salT gene

<400> SEQUENCE: 28

```
gctagcagag atgacgctgg tgaagattgg tccgtggggc ggaaatggag ggtcagctca      60
ggacatcagt gtgccaccca agaagctgtt aggcgtgaca atctacagct cagatgcaat     120
cagatccatt gccttcaact acatcggtgt ggatggacag gaatatgcca ttggtccatg     180
gggtggggc gaaggcacct ctacagagat taaactgggc tcctctgagc agatcaagga     240
gatttctgga acccatggcc cagtctatga tctggctgac attgtcacct atcttaagat     300
```

```
tgtgacaaag tgctaataat acatacgagg ctggagtccc aaatggaaag gaattcagca      360
ttccacttgc aagactctgg cctgtcgttg gatctttgga aggtctggaa cgc            413
```

The invention clamed is:

1. An isolated nucleic acid molecule which comprises the nucleotide sequence as shown in SEQ ID NO: 3 encoding the OsDREB1B protein.

2. An isolated nucleic acid molecule encoding a protein which comprises the amino acid sequence as shown in SEQ ID NO: 4.

3. A recombinant vector comprising the nucleic acid molecule according to claim 1.

4. An isolated host cell transformed with the recombinant vector according to claim 3.

5. A transgenic plant transformed with the recombinant vector according to claim 3.

6. A method for producing the OsDREB1B protein which regulates the transcription of genes located downstream of a stress responsive element, wherein the transgenic plant according to claim 5 is cultured in a medium and said protein is recovered from the resultant culture product.

7. The transgenic plant according to claim 5, wherein the plant is a monocotyledonous plant.

8. A method for producing the OsDREB1B protein which regulates the transcription of genes located downstream of a stress responsive element, wherein the transgenic plant according to claim 7 is cultured in a medium and said protein is recovered from the resultant culture product.

9. A recombinant vector comprising the nucleic acid molecule according to claim 1, operably linked downstream of a stress responsive promoter.

10. An isolated host cell transformed with the recombinant vector according to claim 9.

11. A transgenic plant transformed with the recombinant vector according to claim 9, wherein the plant is a monocotyledonous plant.

12. A method for improving the stress tolerance of plants by introducing the nucleic acid molecule according to claim 1 into the plants.

13. A recombinant vector comprising the nucleic acid molecule according to claim 2.

14. An isolated host cell transformed with the recombinant vector according to claim 13.

15. A transgenic plant transformed with the recombinant vector according to claim 13.

16. The transgenic plant according to claim 15, wherein the plant is a monocotyledonous plant.

17. A method for producing the OsDREB1B protein which regulates the transcription of genes located downstream of a stress responsive element, wherein the transgenic plant according to claim 15 is cultured in a medium and said protein is recovered from the resultant culture product.

18. A method for producing the OsDREB1B protein which regulates the transcription of genes located downstream of a stress responsive element, wherein the transgenic plant according to claim 16 is cultured in a medium and said protein is recovered from the resultant culture product.

19. A recombinant vector comprising the nucleic acid molecule according to claim 2, operably linked downstream of a stress responsive promoter.

20. An isolated host cell transformed with the recombinant vector according to claim 19.

21. A transgenic plant transformed with the recombinant vector according to claim 19, wherein the plant is a monocotyledonous plant.

22. A method for improving the stress tolerance of plants by introducing the nucleic acid molecule according to claim 2 into the plants.

* * * * *